(12) United States Patent
Turner et al.

(10) Patent No.: US 10,739,341 B2
(45) Date of Patent: Aug. 11, 2020

(54) APTAMER METHOD

(71) Applicant: OXFORD NANOPORE TECHNOLOGIES LIMITED, Oxford (GB)

(72) Inventors: Daniel John Turner, Oxford (GB); Daniel George Fordham, Oxford (GB); Roger Charles Gill, Oxford (GB); Clive Gavin Brown, Oxford (GB); Stuart Reid, Oxford (GB); James Anthony Clarke, Oxford (GB); James White, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 197 days.

(21) Appl. No.: 14/378,929

(22) PCT Filed: Feb. 14, 2013

(86) PCT No.: PCT/GB2013/050348
§ 371 (c)(1),
(2) Date: Aug. 14, 2014

(87) PCT Pub. No.: WO2013/121201
PCT Pub. Date: Aug. 22, 2013

(65) Prior Publication Data
US 2015/0177237 A1    Jun. 25, 2015

Related U.S. Application Data

(60) Provisional application No. 61/599,240, filed on Feb. 15, 2012.

(51) Int. Cl.
| | | |
|---|---|---|
| *G01N 33/00* | (2006.01) | |
| *G01N 33/543* | (2006.01) | |
| *G01N 33/53* | (2006.01) | |
| *C12N 15/115* | (2010.01) | |
| *C07H 21/04* | (2006.01) | |

(52) U.S. Cl.
CPC ..... *G01N 33/54386* (2013.01); *C12N 15/115* (2013.01); *G01N 33/5308* (2013.01); *G01N 2333/36* (2013.01); *G01N 2333/49* (2013.01); *G01N 2333/705* (2013.01); *G01N 2333/96463* (2013.01)

(58) Field of Classification Search
None
See application file for complete search history.

(56) References Cited

U.S. PATENT DOCUMENTS

| | | | |
|---|---|---|---|
| 5,576,204 A | 11/1996 | Blanco et al. | |
| 6,426,231 B1 | 7/2002 | Bayley et al. | |
| 6,617,113 B2 | 9/2003 | Deamer et al. | |
| 8,105,846 B2 | 1/2012 | Bayley et al. | |
| 8,828,208 B2 | 9/2014 | Canas et al. | |
| 9,057,102 B2 | 6/2015 | Turner et al. | |
| 9,546,400 B2 | 1/2017 | Turner et al. | |
| 9,551,023 B2 | 1/2017 | Turner et al. | |
| 9,556,480 B2 | 1/2017 | Turner et al. | |
| 9,678,056 B2 | 6/2017 | Turner et al. | |
| 9,738,929 B2 | 8/2017 | Turner et al. | |
| 9,995,728 B2 | 6/2018 | Fordham et al. | |
| 10,480,026 B2 | 11/2019 | Garalde et al. | |
| 2002/0197618 A1 | 12/2002 | Sampson | |
| 2003/0080042 A1* | 5/2003 | Barth | B01D 67/0058 210/321.84 |
| 2004/0029158 A1 | 2/2004 | Olson et al. | |
| 2004/0058378 A1 | 3/2004 | Kong et al. | |
| 2005/0014162 A1 | 1/2005 | Barth et al. | |
| 2006/0014172 A1* | 1/2006 | Muller | B82Y 5/00 435/6.11 |
| 2006/0063171 A1 | 3/2006 | Akeson et al. | |
| 2007/0190543 A1* | 8/2007 | Livak | C12Q 1/6816 435/6.19 |
| 2007/0224613 A1* | 9/2007 | Strathmann | C12Q 1/6869 435/6.11 |
| 2010/0111922 A1 | 5/2010 | Gibori et al. | |
| 2010/0196203 A1 | 8/2010 | Sanghera et al. | |
| 2010/0291548 A1* | 11/2010 | Sharaf | C12Q 1/6816 435/6.11 |
| 2010/0304991 A1* | 12/2010 | Brown | C12N 15/1048 506/9 |
| 2011/0118187 A1* | 5/2011 | Sullenger | A61K 38/177 514/13.8 |

(Continued)

FOREIGN PATENT DOCUMENTS

| | | |
|---|---|---|
| JP | 2010-524436 A | 7/2010 |
| JP | 2014-506575 A | 3/2014 |
| WO | 00/28312 A1 | 5/2000 |
| WO | WO 2005/124888 | 12/2005 |
| WO | 2006/100484 A2 | 9/2006 |
| WO | 2008/102120 A1 | 8/2008 |
| WO | 2008/102121 A1 | 8/2008 |
| WO | 2008/124107 A1 | 10/2008 |
| WO | 2009/035647 A1 | 3/2009 |
| WO | 2009/077734 A2 | 6/2009 |
| WO | WO 2009/046149 | 6/2009 |

(Continued)

OTHER PUBLICATIONS

"How many species of bacteria are there?", WiseGeek.com, accessed Jan. 21, 2014.*

(Continued)

*Primary Examiner* — Bradley L. Sisson
(74) *Attorney, Agent, or Firm* — Wolf, Greenfield & Sacks, P.C.

(57) ABSTRACT

The invention relates to a new method of determining in a sample the presence or absence of one or more analyte members of a group of two or more analytes. The invention therefore relates to a multiplex assay for determining the presence or absence of each analyte in a group of multiple analytes. The assay uses aptamers and transmembrane pores.

6 Claims, 18 Drawing Sheets

Specification includes a Sequence Listing.

(56) References Cited

U.S. PATENT DOCUMENTS

| | | | |
|---|---|---|---|
| 2011/0120871 | A1 | 5/2011 | Reid et al. |
| 2011/0121840 | A1 | 5/2011 | Sanghera et al. |
| 2011/0177498 | A1 | 7/2011 | Clarke et al. |
| 2011/0229877 | A1 | 9/2011 | Jayasinghe et al. |
| 2011/0250705 | A1* | 10/2011 | Polonsky ......... G01N 33/48721 436/518 |
| 2011/0263459 | A1* | 10/2011 | Borer ................ C12N 15/1048 506/16 |
| 2011/0287557 | A1* | 11/2011 | Zhang ................ C12Q 1/6825 436/501 |
| 2012/0025414 | A1* | 2/2012 | Schmidt ................ B82Y 40/00 264/212 |
| 2012/0058468 | A1 | 3/2012 | McKeown |
| 2012/0100530 | A1 | 4/2012 | Moysey et al. |
| 2012/0107802 | A1 | 5/2012 | Stoddart et al. |
| 2012/0322679 | A1 | 12/2012 | Brown et al. |
| 2013/0116130 | A1 | 5/2013 | Fu et al. |
| 2014/0051069 | A1 | 2/2014 | Jayasinghe et al. |
| 2014/0186823 | A1 | 7/2014 | Clarke et al. |
| 2014/0296083 | A1 | 10/2014 | Brown et al. |
| 2015/0008126 | A1 | 1/2015 | Maglia et al. |
| 2015/0031020 | A1 | 1/2015 | Jayasinghe et al. |
| 2015/0152492 | A1 | 6/2015 | Brown et al. |
| 2015/0177237 | A1 | 6/2015 | Turner et al. |
| 2015/0247183 | A1 | 9/2015 | Turner et al. |
| 2015/0301015 | A1 | 10/2015 | Fordham et al. |
| 2016/0010147 | A1 | 1/2016 | Heron et al. |
| 2016/0251710 | A1 | 9/2016 | Brown et al. |
| 2016/0257942 | A1 | 9/2016 | Bruce et al. |
| 2017/0253923 | A1 | 9/2017 | Garalde et al. |

FOREIGN PATENT DOCUMENTS

| | | |
|---|---|---|
| WO | 2010/004265 A1 | 1/2010 |
| WO | 2010/004273 A1 | 1/2010 |
| WO | 2010/086603 A1 | 8/2010 |
| WO | WO 2010/109197 | 9/2010 |
| WO | 2010/122293 A1 | 10/2010 |
| WO | 2011/067559 A1 | 6/2011 |
| WO | WO 2011/103424 A2 | 8/2011 |
| WO | WO 2012/009578 | 1/2012 |
| WO | WO 2012/033524 | 3/2012 |
| WO | WO 2012/088339 A2 | 6/2012 |
| WO | WO 2012/107778 A2 | 8/2012 |
| WO | WO 2012/129242 A2 | 9/2012 |
| WO | WO 2012/164270 A1 | 12/2012 |
| WO | WO 2013/014451 A1 | 1/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/041337 A1 | 3/2014 |
| WO | WO 2014/072703 A1 | 5/2014 |
| WO | WO 2014/135838 A1 | 9/2014 |
| WO | WO 2015/055981 A2 | 4/2015 |
| WO | WO 2015/056028 A1 | 4/2015 |
| WO | WO 2015/110777 A1 | 7/2015 |
| WO | WO 2015/150786 A1 | 10/2015 |

OTHER PUBLICATIONS

"List of sequenced bacterial genomes", Wikipedia.com; accessed Jan. 24, 2014.*

"How many species of bacteria are there?" WiseGeek.com, accessed Jan. 21, 2014. (Year: 2014).*

"List of sequenced bacterial genomes", Wikipedia.com; accessed Jan. 24, 2014. (Year: 2014).*

"Generation of Species Cross-reactive Aptamers Using 'Toggle' SELEX", White et al., Molecular Therapy, vol. 4, No. 6, Dec. 2001, pp. 567-573. (Year: 2001).*

"Aptamer", Wikipedia.com, accessed Nov. 3, 2019. (Year: 2019).*

"Aptamer", Meriam-Webster.com; accessed Nov. 13, 2019. (Year: 2019).*

Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.

Manrao et al., Reading DNA at single-nucleotide resolution with a mutant MspA nanopore and phi29 DNA polymerase. Nat Biotechnol. Apr. 2012;30(4):349-53. doi: 10.1038/nbt.2171. Epub Mar. 25, 2012.

Actis, Paolo et al., "Reversible thrombin detection by aptamer functionalized STING sensors," Biosensors and Bioelectronics, vol. 26:4503-4507 (2011).

Altschul, Stephen F., "A Protein Alignment Scoring System Sensitive at All Evolutionary Distances," J. Mol. Evol., vol. 36:290-300 (1993).

Altschul, Stephen F. et al., "Basic Local Alignment Search Tool," J. Mol. Biol., vol. 215:403-410 (1990).

Anderson, N. Leigh, "The Clinical Plasma Proteome: A Survey of Clinical Assays for Proteins in Plasma and Serum," Clinical Chemistry, vol. 56(2):177-185 (2010).

Berezovski, Maxim et al., "Non-SELEX Selection of Aptamers," J. Am. Chem. Soc., vol. 128:1410-1411 (2006).

Bock, Louis C. et al., "Selection of single-stranded DNA molecules that bind and inhibit human thrombin," Nature, vol. 355:564-566 (1992).

Braha, Orit et al., "Designed protein pores as components for biosensors," Chemistry & Biology, vol. 4:497-505 (1997).

Chandler, Emily L. et al., "Membrane Surface Dynamics of DNA-Threaded Nanopores Revealed by Simultaneous Single-Molecule Optical and Ensemble Electrical Recording," Langmuir, vol. 20:898-905 (2004).

Devereux, John et al., "A comprehensive set of sequence analysis programs for the VAX," Nucleic Acids Research, vol. 12(1):387-395 (1984).

Edwards, Alistair V.G. et al., "The Role of Proteomics in Clinical Cardiovascular Biomarker Discovery," Molecular and Cellular Proteomics, vol. 7:1824-1837 (2008).

Gonzalez-Perez, Alfredo et al., "Biomimetic Triblock Copolymer Membrane Arrays: A Stable Template for Functional Membrane Proteins," Langmuir, vol. 25(18):10447-10450 (2009).

Grant, Gian Paola G. et al., "A facile method for attaching nitroxide spin labels at the 5' terminus of nucleic acids," Nucleic Acids Research, vol. 35(10):e77, 8 pages, doi:10.1093/nar/gkm240 (2007).

Hall, Adam R. et al., "Hybrid pore formation by directed insertion of alpha hemolysin into solid-state nanopores," Nat. Nanotechnol., vol. 5(12):874-877 (2010).

Holden, Matthew A. et al., "Functional Bionetworks from Nanoliter Water Droplets," J. Am. Chem. Soc., vol. 129:8650-8655 (2007).

Jacquet, Sebastien et al., "Identification of Cardiac Myosin-binding Protein C as a Candidate Biomarker of Myocardial Infarction by Proteomics Analysis," Molecular & Cellular Proteomics, vol. 8:2687-2699 (2009).

Kozarewa, Iwanka et al., "96-Plex Molecular Barcoding for the Illumina Genome Analyzer," High-Throughput Next Generation Sequencing: Methods and Applications, Methods in Molecular Biology, Young Min Kown (Ed.), vol. 733, Springer Science+Business Media, LLC, Chapter 20, pp. 279-298 (2011).

Kumar, Abhay et al., "Nonradioactive Labeling of Synthetic Oligonucleotide Probes with Terminal Deoxynucleotidyl Transferase," Analytical Biochemistry, vol. 169:376-382 (1988).

Lieberman, Kate R. et al., "Processive Replication of Single DNA Molecules in a Nanopore Catalyzed by phi29 DNA Polymerase," J. Am. Chem. Soc., vol. 132:17961-17972 (2010).

Montal, M. et al., "Formation of Biomolecular Membranes from Lipid Monolayers and a Study of Their Electrical Properties," Proc. Natl. Acad. Sci. USA, vol. 69(12):3561-3566 (1972).

Nikolov, Vesselin et al., "Behavior of Giant Vesicles with Anchored DNA Molecules," Biophysical Journal, vol. 92:4356-4368 (2007).

Pfeiffer, Indriati et al., "Bivalent Cholesterol-Based Coupling of Oligonucleotides to Lipid Membrane Assemblies," J. Am. Chem. Soc., vol. 126:10224-10225 (2004).

(56) References Cited

OTHER PUBLICATIONS

Rotem, Dvir et al., "Protein Detection by Nanopores Equipped with Aptamers," Journal of the American Chemical Society, vol. 134:2781-2787 (2012).
Stoddart, David et al., "Single-nucleotide discrimination in immobilized DNA oligonucleotides with a biological nanopore," PNAS, doi/10.1073/pnas.0901054106, 6 pages (2009).
Stoltenburg, Regina et al., "SELEX-A (r)evolutionary method to generate high-affinity nucleic acid ligands," Biomolecular Engineering, vol. 24:381-403 (2007).
Troutt, Anthony B. et al., "Ligation-anchored PCR: A simple amplification technique with single-sided specificity," Proc. Natl. Acad. Sci. USA, vol. 89:9823-9825 (1992).
Tuerk, Craig et al., "Systematic Evolution of Ligands by Exponential Enrichment: RNA Ligands to Bacteriophage T4 DNA Polymerase," Science, vol. 249:505-510 (1990).
Van Lengerich, Bettina et al., "Covalent Attachment of Lipid Vesicles to a Fluid-Supported Bilayer Allows Observation of DNA-Mediated Vesicle Interactions," Langmuir, vol. 26(11):8666-8672 (2010).
White, Rebekah et al., "Generation of Species Cross-reactive Aptamers Using 'Toggle' SELEX," Molecular Therapy, vol. 4(6):567-573 (2001).
Yoshina-Ishii, Chiaki et al., "Arrays of Mobile Tethered Vesicles on Supported Lipid Bilayers," J. Am. Chem. Soc., vol. 125:3696-3697 (2003).
Altschul, A protein alignment scoring system sensitive at all evolutionary distances. J Mol Evol. Mar. 1993;36(3):290-300.
Ayub et al., Individual RNA base recognition in immobilized oligonucleotides using a protein nanopore. Nano Lett. Nov. 14, 2012;12(11):5637-43. doi: 10.1021/nl3027873. Epub Oct. 19, 2012.
Barshack et al., Differential diagnosis of hepatocellular carcinoma from metastatic tumors in the liver using microRNA expression. Int J Biochem Cell Biol. Aug. 2010;42(8):1355-62. doi:10.1016/j.biocel.2009.02.021. Epub Mar. 6, 2009.
Branton et al., The potential and challenges of nanopore sequencing. Nat Biotechnol. Oct. 2008;26(10):1146-53. doi:10.1038/nbt.1495.
Chen et al., Highly sensitive and specific microRNA expression profiling using BeadArray technology. Nucleic Acids Res. Aug. 2008;36(14):e87. doi:10.1093/nar/gkn387. Epub Jun. 25, 2008.
Chen et al., Real-time quantification of microRNAs by stem-loop RT-PCR. Nucleic Acids Res. Nov. 27, 2005;33(20):e179.
Cissell et al., Bioluminescence-based detection of microRNA, miR21 in breast cancer cells. Anal Chem. Apr. 1, 2008;80(7):2319-25. doi: 10.1021/ac702577a. Epub Feb. 27, 2008.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Deamer, Nanopore analysis of nucleic acids bound to exonucleases and polymerases. Annu Rev Biophys. 2010;39:79-90. doi:10.1146/annurev.biophys.093008.131250.
Dong et al., Wza the translocon for E. coli capsular polysaccharides defines a new class of membrane protein. Nature. Nov. 9, 2006;444(7116):226-9.
Eliseev et al., Molecular Recognition of Nucleotides, Nucleosides, and Sugars by Aminocyclodextrins. J. Am. Chem. Soc., vol. 116:6081-6088 (1994).
Esquela-Kerscher et al., Oncomirs—microRNAs with a role in cancer. Nat Rev Cancer. Apr. 2006;6(4):259-69.
Gilad et al., Serum microRNAs are promising novel biomarkers. PLoS One. Sep. 5, 2008;3(9):e3148. doi:10.1371/journal.pone.0003148.
Gu et al., Detection of miRNAs with a nanopore single-molecule counter. Expert Rev Mol Diagn. Jul. 2012;12(6):573-84. doi: 10.1586/erm.12.58.
Gu et al., Single molecule sensing by nanopores and nanopore devices. Analyst. Mar. 2010;135(3):441-51. doi: 10.1039/b907735a. Epub Dec. 22, 2009.

Holden et al., Direct introduction of single protein channels and pores into lipid bilayers. J Am Chem Soc. May 11, 2005;127(18):6502-3.
Hornblower et al., Single-molecule analysis of DNA-protein complexes using nanopores. Nat Methods. Apr. 2007;4(4):315-7. Epub Mar. 4, 2007.
Ivanov et al., DNA tunneling detector embedded in a nanopore. Nano Lett. Jan. 12, 2011;11(1):279-85. doi: 10.1021/n1103873a. Epub Dec. 6, 2010.
Jiang et al., miR2Disease: a manually curated database for microRNA deregulation in human disease. Nucleic Acids Res. Jan. 2009;37(Database issue):D98-104. doi:10.1093/nar/gkn714. Epub Oct. 15, 2008.
Kankia et al., Folding of the thrombin aptamer into a G-quadruplex with Sr(2+): stability, heat, and hydration. J Am Chem Soc. Nov. 7, 2001;123(44):10799-804.
Keller et al., Toward the blood-borne miRNome of human diseases. Nat Methods. Sep. 4, 2011;8(10):841-3. doi: 10.1038/nmeth.1682.
Khan et al., Quantitative analysis of microRNA in blood serum with protein-facilitated affinity capillary electrophoresis. Anal Chem. Aug. 15, 2011;83(16):6196-201. doi: 10.1021/ac2016213. Epub Jul. 18, 2011.
Kirschner et al., Haemolysis during sample preparation alters microRNA content of plasma. PLoS One. 2011;6(9):e24145. doi: 10.1371/journal.pone.0024145. Epub Sep. 1, 2011.
Krichevsky et al., A microRNA array reveals extensive regulation of microRNAs during brain development. RNA. Oct. 2003;9(10):1274-81. Erratum in: RNA. Mar. 2004;10(3):551.
Lee et al., The C. elegans heterochronic gene lin-4 encodes small RNAs with antisense complementarity to lin-14. Cell. Dec. 3, 1993;75(5):843-54.
Lewis et al., Conserved seed pairing, often flanked by adenosines, indicates that thousands of human genes are microRNA targets. Cell. Jan. 14, 2005;120(1):15-20.
Loakes, Survey and summary: The applications of universal DNA base analogues. Nucleic Acids Res. Jun. 15, 2001;29(12):2437-47.
Lu et al., MicroRNA expression profiles classify human cancers. Nature. Jun. 9, 2005;435(7043):834-8.
Marathias et al., Structures of the potassium-saturated, 2:1, and intermediate, 1:1, forms of a quadruplex DNA. Nucleic Acids Res. May 1, 2000;28(9):1969-77.
Marusic et al., Solution-state structure of an intramolecular G-quadruplex with propeller, diagonal and edgewise loops . (2012) Nucleic Acids Research, 1-11.
Movileanu, Interrogating single proteins through nanopores: challenges and opportunities. Trends Biotechnol. Jun. 2009;27(6):333-41. doi:10.1016/j.tibtech.2009.02.008. Epub Apr. 23, 2009.
Murphy et al., Reliability of real-time reverse-transcription PCR in clinical diagnostics: gold standard or substandard? Expert Rev Mol Diagn. Mar. 2009;9(2):187-97. doi: 10.1586/14737159.9.2.187.
Nasheri et al., An enzyme-linked assay for the rapid quantification of microRNAs based on the viral suppressor of RNA silencing protein p19. Anal Biochem. May 15, 2011;412(2):165-72. doi: 10.1016/j.ab.2011.01.030. Epub Feb. 1, 2011.
Reinhart et al., MicroRNAs in plants. Genes Dev. Jul. 1, 2002;16(13):1616-26. Erratum in: Genes Dev Sep. 1, 2002;16(17):2313.
Rosenfeld et al., MicroRNAs accurately identify cancer tissue origin. Nat Biotechnol. Apr. 2008;26(4):462-9. doi:10.1038/nbt1392. Epub Mar. 23, 2008.
Shim et al., Single-molecule detection of folding and unfolding of the G-quadruplex aptamer in a nanopore nanocavity. Nucleic Acids Res. Feb. 2009;37(3):972-82. doi: 10.1093/nar/gkn968. Epub Dec. 26, 2008.
Soni et al., Synchronous optical and electrical detection of biomolecules traversing through solid-state nanopores. Rev Sci Instrum. Jan. 2010;81(1):014301. doi: 10.1063/1.3277116.
Tazi et al., Alternative splicing and disease. Biochim Biophys Acta. Jan. 2009;1792(1):14-26. doi: 10.1016/j.bbadis.2008.09.017. Epub Oct. 17, 2008.
Tian et al., Designing a polycationic probe for simultaneous enrichment and detection of microRNAs in a nanopore. ACS Nano. May 28, 2013;7(5):3962-9. doi: 10.1021/nn305789z. Epub Apr. 10, 2013.
Van Heel et al., Single-particle electron cryo-microscopy:towards atomic resolution. Q Rev Biophys. Nov. 2000;33(4):307-69.

(56) References Cited

OTHER PUBLICATIONS

Venkatesan et al., Nanopore sensors for nucleic acid analysis. Nat Nanotechnol. Sep. 18, 2011;6(10):615-24. doi: 10.1038/nnano.2011.129.

Wang et al., Nanopore-based detection of circulating microRNAs in lung cancer patients. Nat Nanotechnol. Sep. 4, 2011;6(10):668-74. doi: 10.1038/nnano.2011.147.

Wang et al., Serum miR-146a and miR-223 as potential new biomarkers for sepsis. Biochem Biophys Res Commun. Mar. 26, 2010;394(1):184-8. doi: 10.1016/j.bbrc.2010.02.145. Epub Feb. 24, 2010.

Wanunu et al., Rapid electronic detection of probe-specific microRNAs using thin nanopore sensors. Nat Nanotechnol. Nov. 2010;5(11):807-14. doi: 10.1038/nnano.2010.202. Epub Oct. 24, 2010.

Wightman et al., Posttranscriptional regulation of the heterochronic gene lin-14 by lin-4 mediates temporal pattern formation in C. elegans. Cell. Dec. 3, 1993;75(5):855-62.

Aquino-Jarquin et al., RNA aptamer evolution: two decades of SELEction. Int J Mol Sci. 2011;12(12):9155-71. doi: 10.3390/ijms12129155. Epub Dec. 8, 2011.

Cheng et al., DNA strand transfer catalyzed by vaccinia topoisomerase:ligation of DNAs containing a 3' mononucleotide overhang. Nucleic Acids Res. May 1, 2000;28(9):1893-8.

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Langecker et al., Synthetic lipid membrane channels formed by designed DNA nanostructures. Science. Nov. 16, 2012;338(6109):932-6. doi: 10.1126/science.1225624.

Sekiguchi et al., Kinetic analysis of DNA and RNA strand transfer reactions catalyzed by vaccinia topoisomerase. J Biol Chem. Jun. 20, 1997;272(25):15721-8.

Shi et al., 5' RACE by tailing a general template-switching oligonucleotide. Biotechniques. Dec. 2000;29(6):1192-5. Erratum in: Biotechniques May 2001;30(5):934.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-LPS Document 13. First Amended Complaint for Patent Infringement. Nov. 30, 2017.

Case 1:17-cv-01353-RGA Document 10. Oxford's opening brief in support of its motion to partially dismiss Pacbio's complaint for patent infringement. Nov. 16, 2017.

United States District Court for the District of Delaware Order. *Pacific Biosciences of California, Inc.* v. *Oxford Nanopore Technolgoies, Inc.* Civil Action No. 17-275-RGA. Nov. 9, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-LPS Document 18. Notice of subsequent events relating to Oxford's motion to dismiss (D.I. 9). Oct. 18, 2017.

Case 1:17-cv-00275-RGA Document 16. Oxford's reply brief in support of its motion to dismiss PacBio's complaint for patent infringement. Jun. 26, 2017.

Case 1:17-cv-00275-RGA Document 14. PacBio's response to Oxford's motion to dismiss. Jun. 5, 2017.

Case 1:17-cv-00275-RGA Document 10. Oxford's opening brief in support of its motion to dismiss PacBio's complaint for patent infringement. May 8, 2017.

Abe et al., Biosensors—Emerging Materials and Applications. Chapter 12: Aptamer Sensors Combined with Enzymes for Highly Sensitive Detection. IntechOpen. 2011. doi: 10.5772/19708. 19 pages.

Manrao et al., Nucleotide discrimination with DNA immobilized in the MspA nanopore. PLoS One. 2011;6(10):e25723. doi: 10.1371/journal.pone.0025723. Epub Oct. 4, 2011.

Nimjee et al., Aptamers: an emerging class of therapeutics. Annu Rev Med. 2005;56:555-83.

Rusconi et al., RNA aptamers as reversible antagonists of coagulation factor IXa. Nature. Sep. 5, 2002;419(6902):90-4.

Song et al., Aptamers and their biological applications. Sensors (Basel). 2012;12(1):612-31. doi: 10.3390/s120100612. Epub Jan. 9, 2012.

U.S. Appl. No. 16/575,610, filed Sep. 19, 219, Garalde et al.

\* cited by examiner

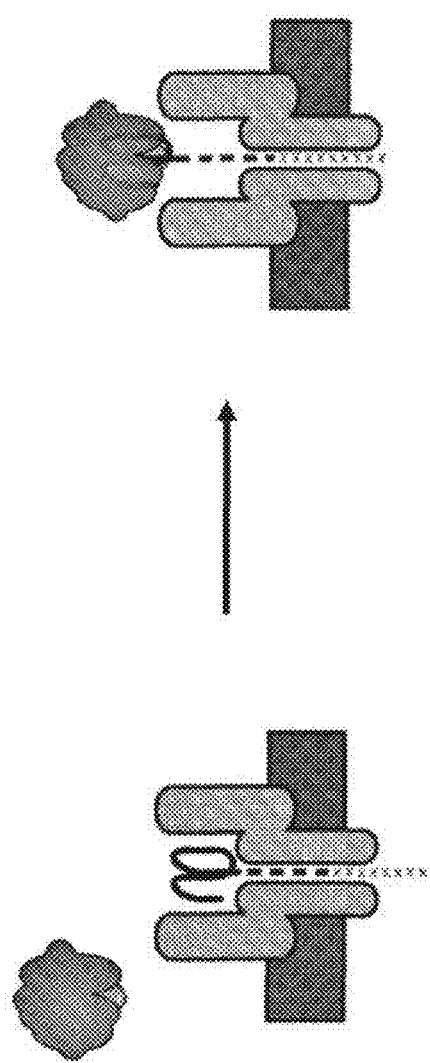
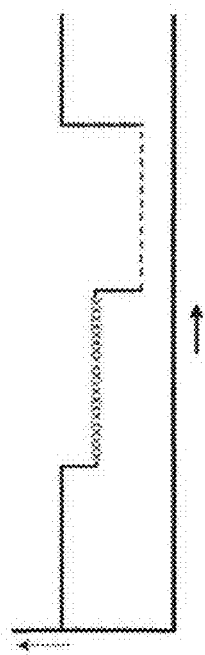
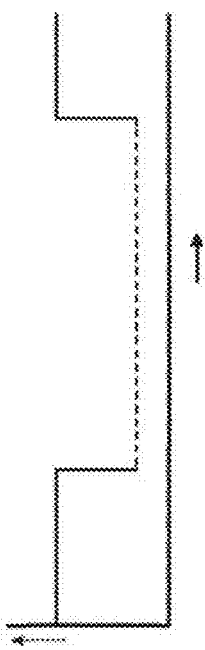
FIG. 1A  FIG. 1B  FIG. 1C  FIG. 1D

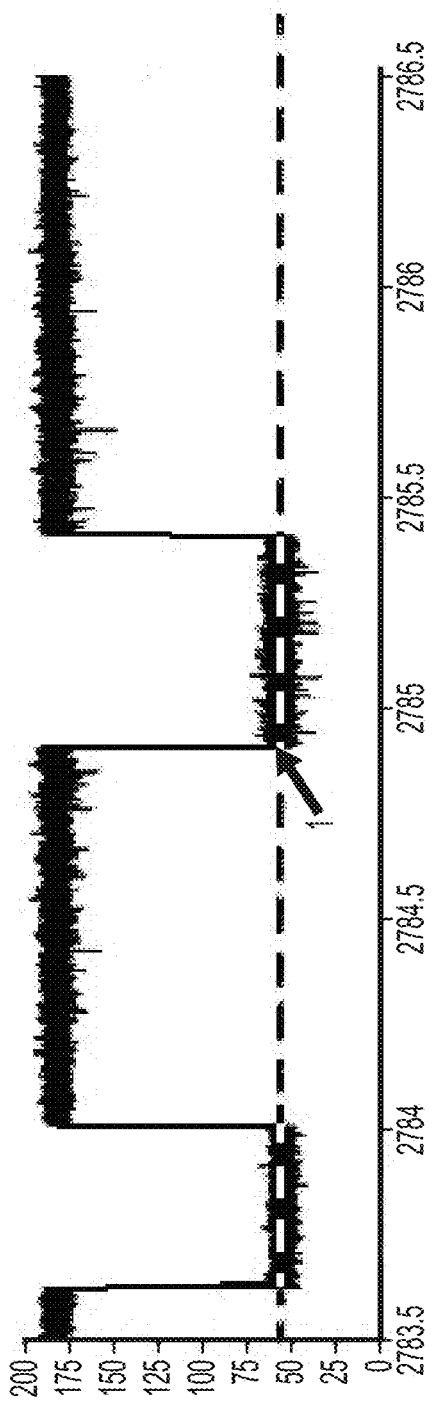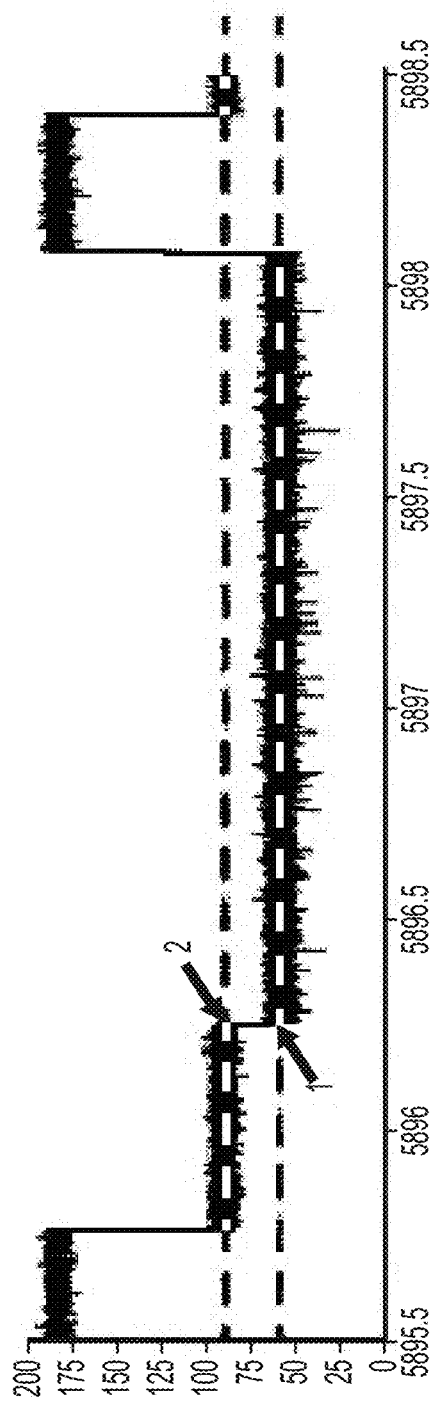
FIG. 2A
FIG. 2B

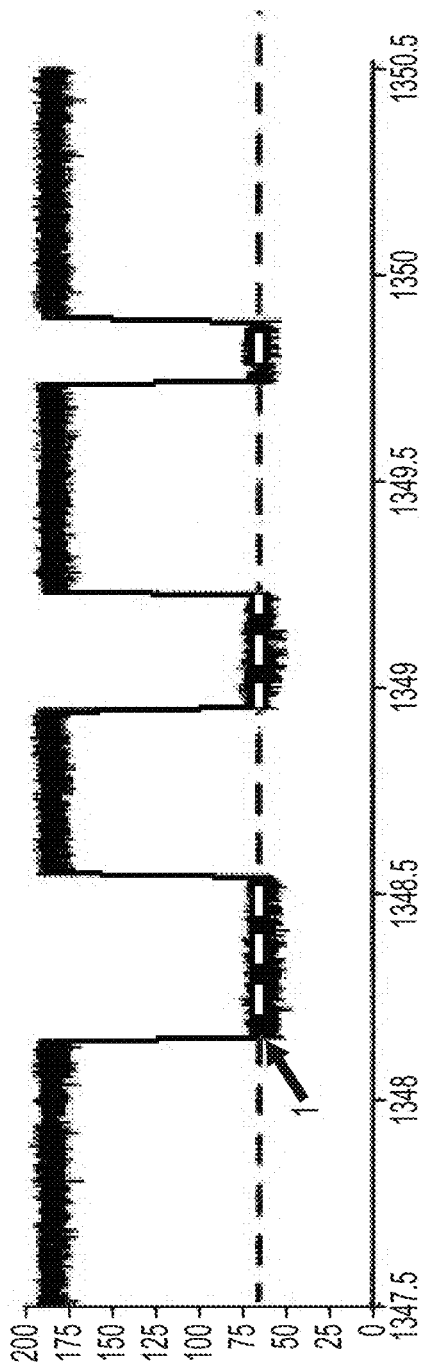
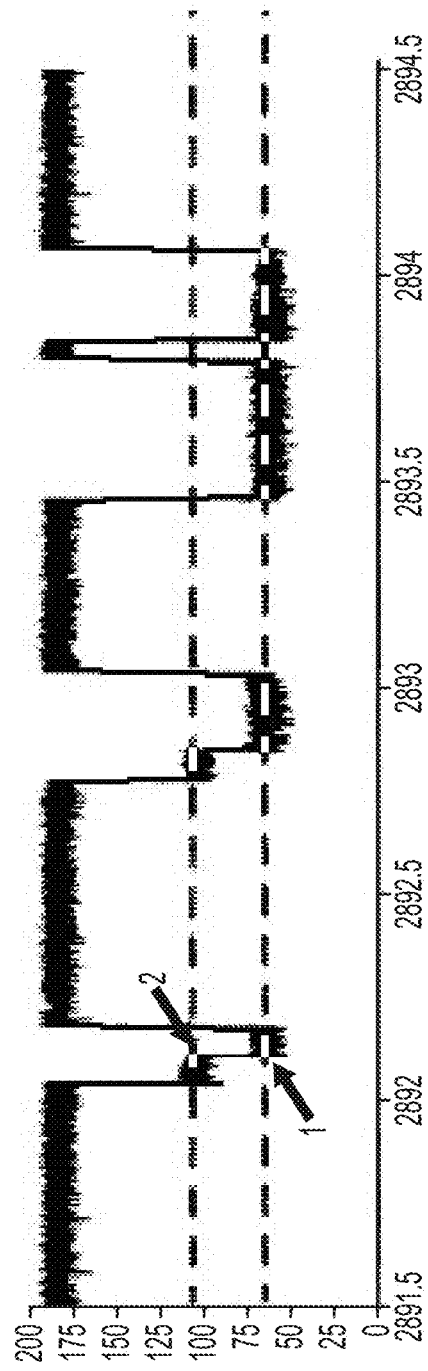
FIG. 4A
FIG. 4B

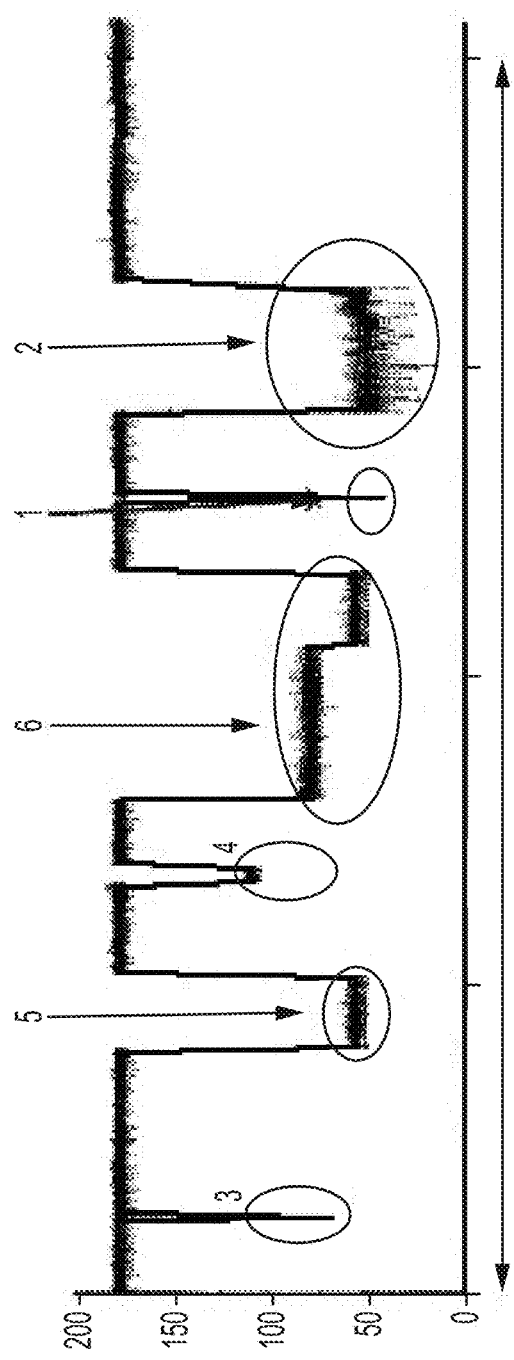
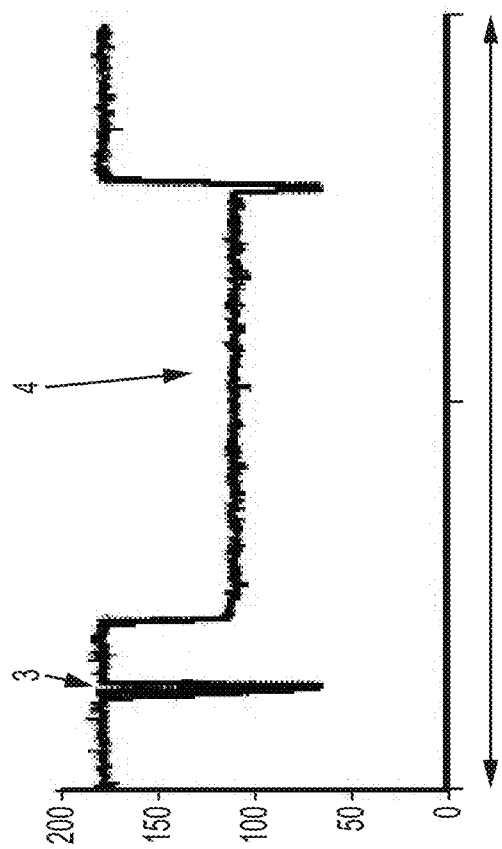
FIG. 12A
FIG. 12B

US 10,739,341 B2

APTAMER METHOD

RELATED APPLICATIONS

This application is a 35 U.S.C. 371 national stage filing of International Application PCT/GB2013/050348, filed 14 Feb. 2013, which claims priority to U.S. Patent Application No. 61/599,240, filed on 15 Feb. 2012. The contents of the aforementioned applications are hereby incorporated by reference.

FIELD OF THE INVENTION

The invention relates to a new method of determining in a sample the presence or absence of one or more analyte members of a group of two or more analytes. The invention therefore relates to a multiplex assay for determining the presence or absence of each analyte in a group of multiple analytes. The assay uses aptamers and transmembrane pores.

BACKGROUND OF THE INVENTION

Transmembrane pores (nanopores) have great potential as direct, electrical biosensors for a variety of analytes, such as polymers and small molecules. When a potential is applied across a nanopore, there is a change in the current flow when a molecule, such as a nucleotide or a polynucleotide, resides transiently in the barrel or channel of the nanopore for a certain period of time. Specific molecules, such as specific nucleotides and specific polynucleotides, give current changes of known signature and duration. Such current changes can be used to identify the nucleotide or polynucleotide present in the pore.

SUMMARY OF THE INVENTION

The inventors have demonstrated that a transmembrane pore can be used in a multiplex assay to determine the presence or absence of each analyte in a group of two or more analytes. More specifically, the inventors have demonstrated that the presence or absence of analytes can be determined using a transmembrane pore and panel of aptamer-containing probes. Each of the analytes of interest is recognised by at least one probe in the panel. Each probe also includes a tail that is capable of entering the pore and affecting the current flowing through the pore. Each tail affects the current flowing through the pore in different and distinctive ways depending on whether or not the probe is bound to one of the analytes of interest. The effect each probe in the panel has on the current flowing through the pore is also distinctive so that the identity of each probe can be detected. This combination of aptamers and tails is such that it is surprisingly possible to identify the binding of one or more of, or even all of, the probes in the panel to the analytes of interest by analyzing the effect of the probe tails on the current flowing through the pore.

Accordingly, the invention provides a method of determining in a sample the presence or absence of one or more analyte members of a group of two or more analytes, the method comprising:

(a) contacting the sample with a transmembrane pore and a panel of two or more probes, wherein each probe recognises one or more of the analyte members and comprises (i) an aptamer that binds to one or more of the analyte members and (ii) a tail which is capable of entering the pore and has different effects on the current flowing through the pore depending on whether or not the aptamer in the probe is bound to one of the analyte members, wherein each probe affects the current flowing through the pore in a distinctive manner, and wherein each analyte member in the group of two or more analytes is recognized by at least one probe in the panel; and (b) measuring the current flowing through the pore to determine which probes in the panel, if any, have bound to an analyte member and thereby determining the presence or absence of one or more analyte members in the sample.

The invention also provides:

a method of determining in a sample the concentration of one or more analyte members of a group of two or more analytes, the method comprising:

(i) carrying out a method of the invention; and (ii) for one or more analyte members shown to be present in the sample comparing the current flowing through the pore in step (b) with control or reference data for each analyte member and thereby determining the concentration of the one or more analyte members in the sample;

a panel of probes for determining in a sample the presence, concentration or absence of one or more analyte members of a group of two or more analytes, the panel comprising two or more probes, wherein each probe recognises one or more of the analyte members and comprises (i) an aptamer that binds to one or more of the analyte members and (ii) a tail which is capable of entering a transmembrane pore and has different effects on the current flowing through the pore depending on whether or not the aptamer in the probe is bound to one of the analyte members, wherein each probe affects the current flowing through the pore in a distinctive manner, and wherein each analyte member in the group of two or more analytes is recognised by at least one probe in the panel;

a kit for determining in a sample the presence, concentration or absence of one or more analyte members of a group of two or more analytes, comprising (a) a panel of probes of the invention and (b) a transmembrane pore; and an analysis apparatus for determining in a sample the presence, concentration or absence of one or more analyte members of a group of two or more analytes, comprising a plurality of pores and a panel of probes of the invention.

DESCRIPTION OF THE FIGURES

FIGS. 1A-1D show a cartoon representation of the probe configuration within the nanopore in the absence (FIG. 1A) and presence (FIG. 1B) of a bound analyte. The expected event traces corresponding to the absence and presence of a bound analyte are shown in FIG. 1C and FIG. 1D, respectively (the y-axis=current and the x-axis=time for FIGS. 1C and 1D). The dashed line represents a poly(dA) region and the cross region represents an abasic region. In this embodiment, when the abasic region is held within the β-barrel of the pore more current flows through the channel than when the poly(dA) region resides within the β-barrel. Transitions from the upper to the lower current level indicate dissociation of the aptamer-analyte complex.

FIGS. 2A-2B illustrate the different block levels that are observed for aptamer sequence 5A15x10A_TBA in the presence (FIG. 2B) and absence (FIG. 2A) of thrombin (the y-axis=current (pA) and the x-axis=time (s) for FIGS. 2A and 2B). In FIG. 2A, level 1 alone is observed when the aptamer (sequence 5A15x10A_TBA) is present in solution in the absence of thrombin. In FIG. 2B, levels 1 and 2 are detected when the aptamer (sequence 5A15x10A_TBA) and thrombin are present in solution (the difference between the levels is 30.5 pA). The appearance of level 2 indicates aptamer bound to thrombin, and transitions from level 2 to level 1 indicate dissociation of the aptamer-thrombin complex.

FIGS. 4A-4B illustrate the different block levels that are observed for aptamer sequence 15X15A_TBA3'CholTEG (SEQ ID NO: 19 which has a cholesterol TEG at the 3' end) is the presence (FIG. 4B) and absence (FIG. 4A) of thrombin (the y-axis=current (pA) and the x-axis=time (s) for FIGS. 4A and 4B). In FIG. 4A, level 1 alone is observed when the aptamer (sequence 15x15A_TBA_3'CholTEG) is present in solution in the absence of thrombin. In FIG. 4B, levels 1 and 2 are detected when the aptamer has been pre-incubated in the presence of thrombin. The appearance of level 2 indicates aptamer bound to thrombin, and transitions from level 2 to level 1 indicate dissociation of the aptamer-protein complex. This experiment was carried out with over a magnitude lower concentration of aptamer than used in Example 2.

FIG. 5A shows the number of events detected for the free aptamer signals (labelled section A) and the signals for each of the different aptamer tails when bound to thrombin (labelled section B). The events for the bound aptamer 15x15A to thrombin is labelled 1, the events for the bound aptamer 17x13A to thrombin is labelled 2, the events for the bound aptamer 19x11A to thrombin is labelled 3 and the events for the bound aptamer 5A15x10A to thrombin is labelled 4. The 'ratio' shown on the x-axis is the current level obtained with the aptamer tail divided by the open pore level (bin size=0.0025) and the y-axis is the count. FIG. 5B (y-axis=current (pA) and x-axis=time (s)) shows the four different block signals detected for each of the aptamer tail sequences (1-4). A separate distinguishable signal is noted for each aptamer.

In FIG. 6A, level 1 alone is observed when the aptamer (sequence 17x8A_PDGF) is present in solution in the absence of PDGF. In FIG. 6B, levels 1 and 2 are detected when the aptamer (sequence 17x8A_PDGF) and PDGF are present in solution. The appearance of level 2 indicates aptamer bound to PDGF, and transitions from level 2 to level 1 indicate dissociation of the aptamer-PDGF complex.

In FIG. 7A, level 1 alone is observed when the aptamer (sequence 25x_PDGF) is present in solution in the absence of PDGF. In FIG. 7B, levels 1 and 3 are detected when the aptamer (sequence 25x_PDGF) and PDGF are present in solution. The appearance of level 3 indicates aptamer bound to PDGF, and transitions from level 3 to level 1 indicate dissociation of the aptamer-PDGF complex.

In FIG. 9A, level 1 alone is observed when the aptamer (sequence 25x_ATP) is present in solution in the absence of ATP. In FIG. 9B, levels 1 and 2 are detected when the aptamer (sequence 25x_ATP) and ATP are present in solution. The appearance of level 2 indicates aptamer bound to ATP, and transitions from level 2 to level 1 indicate dissociation of the aptamer-ATP complex.

In FIG. 10A, level 3 alone is observed when the aptamer (sequence 17x8A_ATP) is present in solution in the absence of ATP. In FIG. 10B, levels 2 and 3 are detected when the aptamer (sequence 17x8A_ATP) and ATP are present in solution. The appearance of level 2 indicates aptamer bound to ATP, and transitions from level 2 to level 3 indicate dissociation of the aptamer-ATP complex.

FIGS. 12A-12B highlight how an array of probes can be used to detect more than one analyte in the same experiment. It is possible to observe both bound and unbound aptamer signals for all three analytes—ATP (ATP aptamer alone=1, ATP aptamer bound to ATP=2), PDGF (PDGF aptamer alone=3, PDGF aptamer bound to PDGF=4), expanded version shown in FIG. 12B and thrombin (thrombin aptamer alone=5, thrombin aptamer bound to thrombin=6). The different analytes can be detected from their characteristic block levels and signal shapes. The y-axis=current in pA for traces in FIGS. 12A and 12B, the x-axis=time for traces in FIGS. 12A and 12B (total trace time for FIG. 12A=4 seconds and total trace time for FIG. 12B=0.1 seconds).

In FIG. 14A, level 1 alone is observed when the aptamer (strep probe 1) is present in solution in the absence of streptavidin. In FIG. 14B, level 2 is detected when the aptamer (strep probe 1) and streptavidin are present in solution.

Description of the Sequence Listing

Figure 3B:
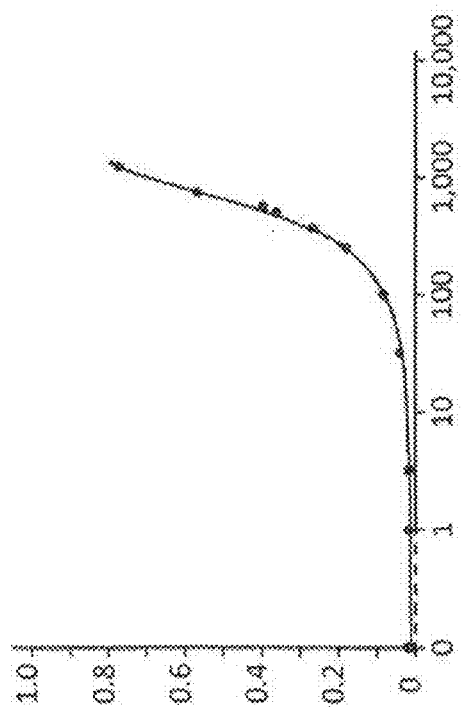
FIGS. 3A-3B illustrate the relationship between the thrombin concentration and the observed event ratio (the number of thrombin bound events only in FIG. 3B compared to the number of thrombin bound and unbound events combined in FIG. 3A). These two graphs show how the ratio between the thrombin bound events and the total number of events (thrombin bound and unbound) vary with the concentration of thrombin. The probe sequence used in this experiment was 5A15x10A_TBA and the final concentration was 1250 nM. Using these calibration graphs it is possible to determine the concentration of thrombin in a sample (graph in FIG. 3A: y-axis=ratio (bound/unbound), x-axis=thrombin concentration (nM), graph in FIG. 3B: y-axis=ratio, x-axis=$\log_{10}$ thrombin concentration (nM)).

SEQ ID NO: 1 shows the polynucleotide sequence encoding one subunit of α-hemolysin-E111N/K 147N (α-HL-NN; (Stoddart, D. S., et al., (2009), *Proceedings of the National Academy of Sciences of the United States of America* 106, p 7702-'7'70'7).

SEQ ID NO: 2 shows the amino acid sequence of one subunit of α-HL-NN.

SEQ ID NO: 3 shows the polynucleotide sequence encoding the LukF subunit of γ-hemolysin.

SEQ ID NO: 4 shows the amino acid sequence of the LukF subunit of γ-hemolysin.

SEQ ID NO: 5 shows the polynucleotide sequence encoding the Hlg2 subunit of γ-hemolysin.

SEQ ID NO: 6 shows the amino acid sequence of the Hlg2 subunit of γ-hemolysin.

SEQ ID NOs: 7 to 24 show the sequences used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a tail" includes two or more such tails, reference to "a polynucleotide" includes two or more such polynucleotides, and the like.

All publications, patents and patent applications cited herein, whether supra or infra, are hereby incorporated by reference in their entirety.

Methods of the Invention

The invention provides a method of determining in a sample the presence or absence of one or more analyte members of a group of two or more analytes. The invention therefore concerns a multiplex assay for each analyte member of a group of analytes. The two or more analytes in the group are predetermined. The invention therefore concerns a multiplex assay for each analyte member of a specific and predetermined group of analytes.

The method comprises contacting the sample with a transmembrane pore and a panel of two or more probes. Each or every probe in the panel recognises one or more of the analyte members and comprises (i) an aptamer that binds to the one or more analyte members and (ii) a tail which is capable of entering the pore and has different effects on the current flowing through the pore depending on whether or not the aptamer in the probe is bound to one of the analyte members. In other words, the tail in each or every probe affects the current flowing through the pore in one way when the aptamer is not bound to one of the analyte members and affects the current flowing through the pore in a different way when the aptamer is bound to the analyte member. This is discussed in more detail below. Each or every probe in the panel also affects the current flowing through the pore in a distinctive manner. This allows a particular probe in the panel to be identified. Since both the identity of a probe and its binding to an analyte member can be measured, the presence of the analyte member can be determined. Each or every analyte member of the group of two or more analytes is recognised by at least one probe in the panel.

The method also comprises measuring the current flowing through the pore to determine which probes in the panel, if any, have bound to an analyte member and thereby determining the presence or absence of one or more analyte members in the sample. The current may be measured using any method known in the art. Specific methods are discussed below.

Steps (a) and (b) are preferably carried out with a potential applied across the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method has several advantages. The method is rapid and cheap compared to existing protein assays, whilst still having high specificity. Probes containing aptamers are quick and cheap to prepare in comparison to, for example, antibodies. The output from the assay is analysed in real time, allowing the assay to be stopped when sufficient information has been obtained. The method allows the detection of multiple analytes from a single sample with minimal or no sample preparation, for example the sample can be blood straight from a patient, thus allowing the method to be carried out by someone with minimal training or qualification. The method can be used to detect many analytes from a single sample, thus obviating the need for multiple tests on a single sample, the number of analytes being limited only by the diversity and number of distinct tails of the probes which can be generated. The method is generally carried out in the presence of unbound aptamers and unbound analyte without the need for washing steps or removal of the unbound entities.

Sample

The sample may be any suitable sample. The invention is typically carried out on a sample that is known to contain or suspected to contain the two or more analytes. The invention may be carried out on a sample that contains two or more analytes whose identity is unknown. Alternatively, the invention may be carried out on a sample to confirm the identity of two or more analytes whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea, coffee.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Analytes

The method of the invention is for determining in a sample the presence or absence of one or more analyte members of a group of two or more analytes. The group of two or more analytes may comprise any number of analytes such as 2, 5, 10, 15, 20, 30, 40, 50, 100 or more analytes. The group preferably has from about 4 to about 100 analytes, such as from about 5 to about 80 analytes, from about 10 to about 60 analytes or from about 20 to about 50 analytes.

The presence or absence of one or more of the analyte members is determined. In other words, for a group of two or more analytes, the method determines whether each of the analyte members in the group is present or absent. One or more, such as 2, 5, 10, 15, 20, 30, 40, 50, 100 or more, of the analyte members may be present and all of the other analyte members in the group may be absent. All of the analyte members may be present. None of the analyte members may be present (i.e. all of the analyte members may be absent). The number of analyte members that are present and the number that are absent are determined using the method of the invention.

The two or more analytes are preferably independently selected from metal ions, inorganic salts, polymers, amino acids, peptides, polypeptides, proteins, nucleotides, oligonucleotides, polynucleotides, dyes, bleaches, pharmaceuticals, diagnostic agents, recreational drugs, explosives and environmental pollutants. The group may comprise two or more analytes of the same type, such as two or more proteins, two or more nucleotides or two or more pharmaceuticals. Alternatively, the group may comprise two or more analytes of different types, such as one or more proteins, one or more nucleotides and one or more pharmaceuticals. The two or more analytes in the group can be analytes that are secreted from cells.

Alternatively, the two or more analytes can be analytes that are present inside cells such that the analyte members must be extracted from the cells before the invention can be carried out.

The two or more analytes in the group are preferably selected from amino acids, peptides, polypeptides and/or proteins. The amino acids, peptides, polypeptides or proteins can be naturally-occurring or non-naturally-occurring. The polypeptides or proteins can include within them synthetic or modified amino acids. A number of different types of modification to amino acids are known in the art. Suitable amino acids and modifications thereof are discussed below with reference to the transmembrane pore. For the purposes of the invention, it is to be understood that the analytes can be modified by any method available in the art.

The proteins can be enzymes, antibodies, hormones, biomarkers, growth factors or growth regulatory proteins, such as cytokines. The cytokines may be selected from interleukins, preferably IFN-1, IL-1, IL-2, IL-4, IL-5, IL-6, IL-10, IL-12 and IL-13, interferons, preferably IL-γ, and other cytokines such as TNF-α. The proteins may be bacterial proteins, fungal proteins, virus proteins or parasite-derived proteins.

The two or more analytes are preferably selected from nucleotides, oligonucleotides and/or polynucleotides. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GNIP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTNIP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-a-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

The polynucleotides may be single stranded or double stranded. At least a portion of the polynucleotide may be double stranded. The polynucleotides can be nucleic acids, such as deoxyribonucleic acid (DNA) or ribonucleic acid (RNA). The polynucleotides can comprise one strand of RNA hybridized to one strand of DNA. The polynucleotides may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotides may comprise any of the nucleotides discussed above, including the modified nucleotides.

The polynucleotides can be any length. For example, the polynucleotides can be at least 10, at least 50, at least 100, at least 150, at least 200, at least 250, at least 300, at least 400 or at least 500 nucleotides or nucleotide pairs in length. The polynucleotides can be 1000 or more nucleotides or nucleotide pairs, 5000 or more nucleotides or nucleotide pairs in length or 100000 or more nucleotides or nucleotide pairs in length.

The group of two or more analytes may be any group of analytes. For instance, the group may be associated with a particular phenotype. The group may be associated with a particular type of cell. For instance, the group may be indicative of a bacterial cell. The group may be indicative of a virus, a fungus or a parasite. The group may be a specific panel of recreational drugs (such as the SAMHSA 5 panel test), of explosives or of environmental pollutants.

The group of two or more analytes is preferably a group of two or more biomarkers that can be used to diagnose or prognose a disease or condition. The biomarkers may be any of the analytes mentioned above, such as proteins or polynucleotides. Suitable panels of biomarkers are known in the art, for example as described in Edwards, A. V. G. et al. (2008) Mol. Cell. Proteomics 7, p 1824-1837; Jacquet, S. et al. (2009), Mol. Cell. Proteomics 8, p 2687-2699; Anderson N. L. et al (2010) Clin. Chem. 56, 177-185. The disease or condition is preferably cancer, coronary heart disease, cardiovascular disease or sepsis.

As discussed in more detail below, the group may comprise two or more analytes in the same class. Analytes are within the same class if they have structural similarity. If the analytes are proteins, they are within the same class if they are in the same Structural Classification of Proteins (SCOP) classification. Analytes are within the same class if they related functionally or related phylogenetically. For instance, the opiates, such as heroin, codeine and morphine, may be considered to be in the same class of analytes. Similarly, the different forms of interleukin 1, such as IL-1α, IL-1β and IL-1RA, may be considered to be in same class of analytes. In the context of the invention, a class of analytes is typically two or more analytes that are different structurally but can be bound by one aptamer. The method preferably comprises the use of at least one probe which comprises an aptamer that binds to the analyte members in a class. For instance, such an embodiment allows the determination of the presence or absence or one or more IL-1 analytes in a sample. The ability to detect the presence or absence of one or more analyte members in a particular class has its advantages. For instance, an initial multiplex assay may be carried out for a variety of classes of analytes. Once the presence of one more classes has been determined, more specific multiplex assays relating to those classes may be carried out to determine the presence or absence of one or more of the analyte members within each class.

Transmembrane Pore

The method of the invention comprises contacting the sample with a transmembrane protein pore. A transmembrane pore is a structure that permits hydrated ions driven by an applied potential to flow from one side of the membrane to the other side of the membrane.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647). An amphiphilic layer may be formed across a solid state pore. This may be described in the art as hybrid pore formation (Hall et al., Nat Nanotechnol., 2010, 5, 874-877). The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

One or more of the probes in the panel are preferably coupled to the membrane. Each probe in the panel is more preferably coupled to the membrane. This may be done using any known method. If the membrane is an amphiphilic layer, such as a lipid bilayer (as discussed in detail above), a probe is preferably coupled to the membrane via a polypeptide present in the membrane or a hydrophobic anchor present in the membrane. The hydrophobic anchor is preferably a lipid, fatty acid, sterol, carbon nanotube or amino acid.

A probe may be coupled directly to the membrane. A probe is preferably coupled to the membrane via a linker. Preferred linkers include, but are not limited to, polymers, such as polynucleotides, polyethylene glycols (PEGs) and polypeptides.

The coupling may be stable or transient. For certain applications, the transient nature of the coupling is preferred. Transient coupling minimises permanent blocking allowing data to be accumulated more quickly as time is not lost in manually unblocking the pore. When permanent coupling is used the amphiphilic layer may be destabilized or it could cause the build up of tethered aptamers on the cis side, thus altering the experimental equilibrium. Theses effects can be minimised by coupling transiently. Chemical groups that form stable or transient links with the membrane are discussed in more detail below. A probe may be transiently coupled to an amphiphilic layer, such as a lipid bilayer using cholesterol or a fatty acyl chain. Any fatty acyl chain having a length of from about 6 to about 30 carbon atoms, such as hexadecanoic acid, may be used.

In preferred embodiments, one or more probes are or each probe is coupled to an amphiphilic layer. Coupling to synthetic lipid bilayers has been carried out previously with various different tethering strategies. These are summarised in Table 1 below.

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Probes may be functionalized using a modified phosphoramidite in the synthesis reaction, which is easily compatible for the addition of reactive groups, such as thiol, cholesterol, lipid and biotin groups. These different attachment chemistries give a suite of attachment options for probes. Each different modification group tethers the probe in a slightly different way and coupling is not always permanent so giving different dwell times for the probe to the bilayer.

Coupling of probes can also be achieved by a number of other means provided that a reactive group can be added to the probe. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A, P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the probe contains a synthetic polynucleotide, the coupling chemistry can be incorporated during the chemical synthesis of the probe. For instance, the probe can be synthesized using a primer with a reactive group attached to it.

A common technique for the amplification of sections of genomic DNA is using polymerase chain reaction (PCR). In this technique, using two synthetic oligonucleotide primers, a number of copies of the same section of DNA can be generated, where for each copy the 5' end of each strand in the duplex will be a synthetic polynucleotide. By using an antisense primer that has a reactive group, such as a cholesterol, thiol, biotin or lipid, each copy of the target DNA amplified will contain a reactive group for coupling.

If the transmembrane pore is a transmembrane protein pore as discussed below, the probes in the panel are preferably not coupled to the pore. If the pore is a protein pore, the probes in the panel are more preferably not covalently attached to the pore.

The transmembrane pore generally comprises a vestibule and a barrel or channel. The barrel or channel is typically a substantially cylindrical passage through which hydrated ions can flow across the membrane. The vestibule typically forms an entrance to the barrel or channel and has a different cross-sectional area from the barrel or channel. Typically the vestibule has a greater cross-sectional area than the barrel. A good example of a pore with a vestibule and a barrel or channel is α-hemolysin (α-HL), which is discussed in more detail below. A pore comprising a vestibule and a barrel or channel can be formed in a solid state layer. The presence of a vestibule is preferred because it facilitates the method of the invention as discussed in more detail below.

The barrel or channel may have any width. Typically, the barrel or channel is sufficiently wide that the tail of each probe can enter the barrel or channel and affect the current flowing through the pore. As discussed in more detail below, the tail preferably comprises a polymer. The barrel or channel is preferably sufficiently wide that the polymer can enter the barrel or channel and affect the current flowing through the pore. In some instances, the tail can comprise a polynucleotide. The barrel or channel is preferably sufficiently narrow that a single stranded polynucleotide can enter and pass through the pore, but a double-stranded polynucleotide cannot enter and pass through the pore.

For the reasons discussed in more detail below, the vestibule is typically wide enough to allow each aptamer in the panel of probes to enter, but narrow enough to prevent each aptamer/analyte member complex from entering. The vestibule and barrel or channel are each typically long enough to contain at least two nucleotides, such at least 5, at least 10, at least 20 nucleotides in total, for example at least 8 in the vestibule and at least 12 in the barrel.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore permits the probes to flow from one side of the membrane, such as a lipid bilayer, to the other as discussed below. The transmembrane protein pore preferably allows a single-stranded polynucleotide, such as ssDNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with the tail, such as polymer units in the tail. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and negatively-charged polymer units, such as nucleotides, in the tail.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore is preferably derived from α-hemolysin (α-HL) or leukocidin.

The pore may be a homo-oligomer (all monomer units identical) or a hetero-oligomer (two or more different types of monomer). The pore may comprise linked monomers, for example dimers.

The pore may comprise at least one dimer and 1, 2, 3, 4, 5, 6, 7 or 8 monomers. The pore may comprise two, three, four or more dimers. Such pores further comprise sufficient monomers to form the pore. A further pore comprises only dimers, for example a pore may comprise 4, 5, 6, 7 or 8 dimers. A specific pore according to the inventions comprises four dimers. The dimers may oligomerise into a pore with a structure such that only one monomer of a dimer contributes to the barrel or vestibule of the pore. Typically the other monomers of the construct will be on the outside of the barrel or vestibule of the pore. For example, a pore may comprise 5, 6, 7 or 8 dimers where the barrel or vestibule comprises 8 monomers.

The transmembrane protein pore is preferably derived from α-hemolysin (α-HL). The wild type α-HL pore is formed of seven identical monomers or subunits (i.e. it is heptameric). The transmembrane protein pore preferably comprises seven monomers derived from α-HL. The sequence of one monomer or subunit of α-hemolysin-NN (i.e. a pore derived from α-HL) is shown in SEQ ID NO: 2. α-hemolysin-NN contains the substitutions E111N and K147N. The transmembrane protein pore preferably comprises seven monomers each comprising the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 2 form part of a constriction of the barrel or channel of α-HL.

The pore preferably comprises seven proteins or monomers each comprising the sequence shown in SEQ ID NO: 2 or a variant thereof. The transmembrane protein is preferably (a) formed of seven identical subunits as shown in SEQ ID NO: 2 or (b) a variant thereof in which one or more of, or all of, the seven subunits is a variant of SEQ ID NO: 2 and which retains pore activity. The seven proteins may be the same (homoheptamer) or different (heteroheptamer).

A variant of SEQ ID NO: 2 is a protein that has an amino acid sequence which varies from that of SEQ ID NO: 2 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

One preferred variant of SEQ ID NO: 2 is the wild-type subunit, i.e. a subunit in which E has been replaced at position 111 and K has been replaced at position 147.

The variant may include modifications that facilitate covalent attachment to or interaction with another molecule. The variant preferably comprises one or more reactive cysteine residues that facilitate attachment. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with polymer units in the tail, such as nucleotides, amino acids or ethylene oxide.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology.

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (www.ncbi.nlm.nih.gov/).

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 200 or 250 amino acids in length. Such fragments may be used to produce the pores. A fragment preferably comprises the pore forming domain of SEQ ID NO: 2. Fragments typically include residues 119, 121, 135, 113 and 139 of SEQ NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from about 1 to about 10 amino acids in length. Alternatively, the extension may be longer, for example up to about 50 or about 100 amino acids. A carrier protein may be fused to an amino acid sequence according to the invention.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of α-HL, which contains a β-barrel, is provided by β-strands in each subunit. A variant of SEQ ID NO: 2 typically comprises the regions in SEQ ID NO: 2 that form β-strands. The amino acids of SEQ ID NO: 2 that form β-strands are discussed above. One or more modifications can be made to the regions of SEQ ID NO: 2 that form β-strands as long as the resulting variant retains its ability to form a pore. Specific modifications that can be made to the β-strand regions of SEQ ID NO: 2 are discussed above.

A variant of SEQ ID NO: 2 preferably includes one or more modifications, such as substitutions, additions or deletions, within its α-helices and/or loop regions. Amino acids that form α-helices and loops are discussed above.

The transmembrane protein pore is also preferably derived from leukocidin. A leukocidin is a hetero-oligomeric pore with two different subunits, one class S subunit and one class F subunit. Suitable leukocidins include, but are not limited to, gamma hemolysin (γ-HL) comprising LukF (HlgB) and Hlg2 (HlgA), leukocidin comprising LukF (HlgB) and LukS(HlgC), leukocidin PV comprising LukF-PV and LukS-PV, LukE/LukD pore comprising LukE and LukD and LukS-I/LukF-I comprising LukF-I and LukS-I.

When the transmembrane protein pore is a leukocidin, it is preferably derived from gamma hemolysin (γ-HL). The wild type γ-HL pore is formed of eight subunits (i.e. it is octameric) and contains four subunits of LukF and four subunits of Hlg2. The sequence of one monomer or subunit of LukF is shown in shown in SEQ ID NO: 4. The sequence of one monomer or subunit of Hlg2 is shown in SEQ ID NO: 6. The transmembrane protein pore preferably comprises four monomers each comprising the sequence shown in SEQ ID NO: 4 or a variant thereof and four monomers each comprising the sequence shown in SEQ ID NO: 6 or a variant thereof. Amino acids 109-147 of SEQ ID NO: 4 and 103-139 of SEQ ID NO: 6 form loop regions.

The γ-hemolysin pore is preferably (a) γ-hemolysin formed of four identical subunits as shown in SEQ ID NO: 4 and four identical subunits as shown in SEQ ID NO: 6 or (b) a variant thereof in which one or more of, or all of, the subunits is a variant of SEQ ID NO: 4 and/or one or more of, or all of, the subunits is a variant of SEQ ID NO: 6 and the pore retains pore activity. Such pores are hetero-octamers.

A variant of SEQ ID NO: 4 or 6 is a protein that has an amino acid sequence which varies from that of SEQ ID NO: 4 or 6 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with another molecule. The variant preferably comprises one or more reactive cysteine residues that facilitate attachment. The variant may also include modifications that facilitate any interaction with polymer units in the tail, such as nucleotides, amino acids or ethylene oxide.

The variant may be a naturally occurring variant which is expressed naturally by an organism, for instance by a

*Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4 or 6, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 or 6 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 or 6 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 or 6 may additionally be deleted from the polypeptides described above. Up to 1, 2, 3, 4, 5, 10, 20 or 30 residues may be deleted, or more.

Variants may be fragments of SEQ ID NO: 4 or 6. Such fragments retain pore-forming activity. Fragments may be at least 50, 100, 200 or 250 amino acids in length. A fragment preferably comprises the pore-forming domain of SEQ ID NO: 4 or 6.

One or more amino acids may be alternatively or additionally added to the polypeptides described above. An extension may be provided at the amino terminus or carboxy terminus of the amino acid sequence of SEQ ID NO: 4 or 6 or a variant or fragment thereof. The extension may be quite short, for example from about 1 to about 10 amino acids in length. Alternatively, the extension may be longer, for example up to about 50 or about 100 amino acids. A carrier protein may be fused to a pore or variant.

As discussed above, a variant of SEQ ID NO: 4 or 6 is a subunit that has an amino acid sequence which varies from that of SEQ ID NO: 4 or 6 and which retains its ability to form a pore. A variant typically contains the regions of SEQ ID NO: 4 or 6 that are responsible for pore formation. The pore forming ability of γ-HL, which contains a β-barrel, is provided by β-strands in each subunit. A variant of SEQ ID NO: 4 or 6 typically comprises the regions in SEQ ID NO: 4 or 6 that form β-strands. The amino acids of SEQ ID NO: 4 or 6 that form β-strands are discussed above. One or more modifications can be made to the regions of SEQ ID NO: 4 or 6 that form β-strands as long as the resulting variant retains its ability to form a pore. Specific modifications that can be made to the β-strand regions of SEQ ID NO: 4 or 6 are discussed above.

A variant of SEQ ID NO: 4 or 6 preferably includes one or more modifications, such as substitutions, additions or deletions, within its α-helices and/or loop regions. Amino acids that form α-helices and loops are discussed above.

In some embodiments, the transmembrane protein pore is chemically modified. The monomers derived from α-HL (i.e. SEQ ID NO: 2 or a variant thereof) or γ-HL (i.e. SEQ ID NO: 4 or 6 or a variant thereof) may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating α-HL hetero-oligomers (Chem Biol. 1997 July; 4(7):497-505).

The monomer derived from α-HL or γ-HL may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

The monomer derived from α-HL or γ-HL may also be produced using D-amino acids. For instance, the monomer derived from α-HL or γ-HL may comprise a mixture of L-amino acids and D-amino acids. This is conventional in the art for producing such proteins or peptides.

The monomer derived from α-HL or γ-HL may contain one or more specific modifications to facilitate interactions with the tails. The monomer derived from α-HL or γ-HL may also contain other non-specific modifications as long as they do not interfere with pore formation. A number of non-specific side chain modifications are known in the art and may be made to the side chains of the monomer derived from α-HL or γ-HL. Such modifications include, for example, reductive alkylation of amino acids by reaction with an aldehyde followed by reduction with $NaBH_4$, amidination with methylacetimidate or acylation with acetic anhydride.

The monomer derived from α-HL or γ-HL can be produced using standard methods known in the art. The monomer derived from α-HL may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The pore can be produced using standard methods known in the art. Polynucleotide sequences encoding a pore may be derived and replicated using standard methods in the art. Polynucleotide sequences encoding a pore may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Panel of Probes

The method of the invention comprises contacting the sample with a panel of two or more probes. In other words, the method of the invention comprises contacting the sample with a panel of two or more types of probe. The panel may comprise any number of two or more probes, such as 2, 5, 10, 15, 20, 30, 40, 50, 100 or more probes. The panel preferably has from about 4 to about 100 probes, such as from about 5 to about 80 probes, from about 10 to about 60 probes or from about 20 to about 50 probes.

The method uses multiple instances of each or every probe in the panel because, if an analyte is present in the sample, there will almost certainly be multiple instances of the analyte in the same. In other words, the method uses multiple instances of each or every type of probe in the panel.

Each or every analyte member of the group of two or more analytes is recognised by at least one probe (i.e. at least one type of probe) in the panel. A probe recognises an analyte member if it provides a positive signal in the method of the invention when the analyte is present in the sample. In other words, a probe recognises an analyte member if it affects the current in a distinctive manner when the analyte is present in the sample. A probe typically recognises an analyte member because it comprises an aptamer that binds the analyte member. The fact that each analyte member is recognised by at least one probe allows the presence or absence of each analyte member in the group to be determined using the method of the invention. The way in which a probe recognises an analyte member is discussed in more detail below.

At least one probe (i.e. at least one type of probe) in the panel preferably recognises a class of analyte members within the group of two or more analytes and comprises an aptamer that binds to the analyte members in the class. The advantages associated with determining the presence or absence of a class of analyte members within the group is discussed above. The production of an aptamer that binds to more than one analyte members is discussed below.

At least one probe in the panel (i.e. at least one type of probe) preferably specifically recognises one of the analyte members and comprises an aptamer that specifically binds to the analyte member. A probe specifically recognises one of the analyte members if it only provides a positive signal in the method of the invention when the analyte is present in the sample. In other words, a probe specifically recognises an analyte member if it only affects the current in a distinctive manner when the analyte is present in the sample. A probe typically specifically recognises an analyte member because it comprises an aptamer that specifically binds the analyte member. Specific binding of aptamers is discussed in more detail below. In this embodiment, at least one probe is targeted to only one analyte member. Each probe (i.e. each type of probe) in the panel more preferably specifically recognises one of the analyte members and comprises an aptamer that specifically binds to the analyte member. In this embodiment, each probe is targeted to only one analyte member. The multiplex assay of the invention is simpler if only one probe is used to detect an analyte member. In particular, it is more straightforward to determine the presence or absence of an analyte member by measuring the distinctive effect of one probe on the current flowing through the pore.

Each probe (i.e. each type of probe) in the panel preferably comprises a different aptamer. In other words, no two probes (i.e. no two types of probe) in the panel comprise the same aptamer. As discussed in more detail below, differences between different aptamers can contribute to the distinctiveness of effect each probe has on the current flowing through the pore. Different aptamers typically bind to different analyte members, but may bind to the same analyte member. In a preferred embodiment, two or more probes in the panel comprise different aptamers that specifically bind to the same analyte member. Two or more probes in the panel preferably comprise different aptamers and the same polynucleotide tail. In this embodiment, the distinctiveness of the effects each probe has on the current flowing through pore is typically provided by the differences between the aptamers.

Each probe (i.e. each type of probe) in the panel preferably comprises a different tail. As discussed in more detail below, the differences between different tails can also contribute to the distinctiveness of the effects each probe has on the current flowing through the pore. Two or more probes in the panel preferably comprise the same aptamer and different tails. In this embodiment, the distinctiveness of the effects each probe has on the current flowing through pore is typically provided by the differences between the tails. In this embodiment, two or more probes are targeted to the same one or more analyte members because they share the same aptamer. This can provide an internal control because positive signals from both probes will be required to conclude that one of the one or more analyte members is present in the sample.

Each probe (i.e. each type of probe) in the panel may comprise a different aptamer and a different polynucleotide tail. In other words, In other words, no two probes (i.e. no two types of probe) in the panel comprise the same aptamer and the same tail. In the embodiment, the different aptamers and different tails typically both contribute to the distinctiveness of the effects each of the two or more probes has on the current flowing through pore.

The number of probes (i.e. types of probes) in the panel is typically the same as or greater than number of analyte members of the group. There may be fewer probes in the panel than the number of analyte members of the group because each probe can recognise one or more analyte members. If the number of probes in the panel is greater than the number of analyte members of the group, two or more probes are targeted to the same one or more analyte members and the method of the invention comprises an internal control as discussed above. The number of probes in the panel is preferably the same as the number of analyte members of the group of two or more analytes. This is the simplest embodiment of the invention, but it does not include an internal control.

Aptamer

Each probe (i.e. each type of probe) in the panel recognises one or more of the analyte members and comprises an aptamer that binds to one or more analyte members. Recognition of analyte members by probes is discussed above.

Aptamers are small molecules that bind to one or more analyte members. Aptamers can be produced using SELEX (Stoltenburg, R. et al., (2007), *Biomolecular Engineering* 24, p 381-403; Tuerk, C. et al., *Science* 249, p 505-510; Bock, L. C. et al., (1992), *Nature* 355, p 564-566) or NON-SELEX (Berezovski, M. et al. (2006), *Journal of the American Chemical Society* 128, p 1410-1411).

The aptamer may be capable of binding to one or more analyte members. In this embodiment, a probe comprising the aptamer is capable of recognising the one or more analyte members. Aptamers that bind to more than one analyte member can be produced using Toggle SELEX (White, R. et al., (2001), *Molecular Therapy* 4, p 567-573). Although an aptamer may be capable of binding to one or more analytes, each aptamer typically binds to only one analyte in the method of the invention. This is discussed in more detail below.

The aptamer preferably binds to a class of analyte members within the group of two or more analytes. A class of analyte members is discussed above. Aptamers that bind to a class of analyte members can be produced using Toggle SELEX.

The aptamer is preferably a peptide aptamer or an oligonucleotide aptamer. The peptide aptamer may comprise any amino acids. The amino acids may be any of those discussed above. The oligonucleotide aptamer may comprise any nucleotides. The nucleotides may be any of those discussed above.

The aptamer can be any length. The aptamer is typically at least 15 amino acids or nucleotides in length, such as from about 15 to about 50, from about 20 to about 40 or from about 25 to about 30 amino acids or nucleotides in length.

Tail

Each probe (i.e. each type of probe) in the panel comprises a tail which is capable of entering the pore. The tail is typically a linear molecule that is capable of entering and passing through the barrel or channel of the pore. Suitable molecules for forming the tail are discussed below. When the tail enters the pore, it affects the current flowing through the pore in a manner that is specific for the part of the tail that is present in the barrel or channel.

The tail has different effects on the current flowing through the pore depending on whether or not the aptamer in the probe is bound to one of the analyte members. The tail in each probe affects the current flowing through the pore in one way when the aptamer is not bound to the analyte member and affects the current flowing through the pore in a different way when the aptamer is bound to the analyte member. This is important because it allows the presence or absence of each analyte member in the group to be determined using the method.

The different effects of the tail on the current flowing through the pore depending on whether or not the aptamer in the probe is bound to one of the analyte members can be measured based on the time it takes for the probe to move through the pore. In other words, the different effects of the tail on the current flowing through the pore depending on whether or not the aptamer in the probe is bound to one of the analyte members can be measured based on the time for which the probe affects the current flowing through the pore. Without wishing to be bound by theory, the tail of each probe enters the barrel or channel of a pore when the panel is contacted with the pore and affects the current flowing through the pore. Multiple instances of the pore are used in the method of the invention. For a short while, the movement of the entire probe through the pore is prevented (i.e. delayed) by the aptamer. Aptamers are typically folded into a three-dimensional structure and so are typically too large to move through the barrel or channel of the pore. After a short while, the aptamer unfolds under the influence of the potential and the entire probe moves through the pore along the potential. Once the probe has passed through the pore, the current flowing through the pore returns to the level seen in the absence of the panel of probes. If the probe's target analyte member is present, the aptamer binds to the analyte member and the aptamer/analyte complex further delays the probe moving through the pore. In this embodiment, the probe moves through the pore more slowly in the presence of the analyte member than in the absence of the analyte member. In other words, the probe affects the current flowing through the pore for more time in the presence of the analyte member than in the absence of the analyte member. In this embodiment, the distinctiveness between probes (i.e. between different types of probes) may be due to one or more, or all, of (1) the different lengths of the probes, (2) the presence or absence of one or more double stranded polynucleotide regions in the tails of each probe and (3) the different binding affinities of the different aptamers in each probe. All three of these can be altered such that each probe affects the current flowing through the pore for a specific amount of time ("dwell time"). The presence of one or more double stranded polynucleotide region may also be used to hold a specific tail region that is indicative of the probe in the barrel or channel as discussed below.

The tail preferably comprises at least two regions that affect the current flowing through the pore in different ways and one region is situated in the pore when the aptamer is not bound to one of the analyte members and a different region is situated in the pore when the aptamer is bound to the analyte member. The at least two regions have different compositions and so affect the current flowing through the pore in different ways. For instance, one region could be a polypeptide and the other could be a polynucleotide or the at least two regions could be polynucleotides having different nucleotide sequences. This is discussed in more detail below.

Control experiments may be carried out to determine the effect the different regions in a tail have on the current flowing through the pore when the probe is bound to one of the analyte members or not. Results from carrying out the method of the invention on a test sample can then be compared with those derived from such control experiments in order to determine whether a particular analyte is present or absent in the test sample.

Again without wishing to be bound by theory, the tail of each probe enters the barrel or channel of a pore when the panel is contacted with the pore and affects the current flowing through the pore. Multiple instances of the pore are used in the method of the invention. For a short while, the movement of the entire probe through the pore is prevented by the aptamer because, as discussed above, folded aptamers are typically too large to move through the barrel or channel of the pore. If the probe's target analyte member is not present, the aptamer is not bound to an analyte member and one region (the first region) of the tail is typically held in the barrel or channel as the aptamer prevents the movement of the probe through the pore. This first region affects the current flowing through the pore in a particular way based on the composition of the region. After a short while, the aptamer unfolds under the influence of the potential and the entire probe moves through the pore along the potential. Once the probe has passed through the pore, the current flowing through the pore returns to the level seen in the absence of the panel of probes.

If the probe's target analyte member is present in the sample, the tail of each probe still enters the barrel or channel of the pore as discussed above, but the aptamer/analyte member complex typically prevents the tail entering as far as if the analyte member was not present.

Hence, a different region of the tail (the second region) is held in the barrel or channel and affects the current flowing through the pore in a different way from the first region. After a short while, the aptamer unfolds under the influence of the potential, releases the analyte member and the entire probe moves through pore. As the probe moves through the pore, the first region will follow the second region through the barrel or channel and for a short while will affect the current flowing through the pore as if the analyte member is not present. Once the probe has passed through the pore, the current flowing through the pore returns to the level seen in the absence of the panel of probes. An example of this is shown in cartoon form in FIGS. 1A-1D.

In this embodiment, the distinctiveness between probes (i.e. between different types of probes) may be due to one or more, or all, of (1) the different lengths of the probes, (2) the presence or absence of one or more double stranded polynucleotide regions in the tails of each probe, (3) the different binding affinities of the different aptamers in each probe and (4) differences between the at least two regions in each probe. 1 to 3 can be altered such that each probe affects the current flowing through the pore for a specific amount of time ("dwell time"). The presence of one or more double stranded polynucleotide region may also be used to hold a specific tail region that is indicative of the probe in the barrel or channel as discussed below.

The at least two regions in each probe can be designed such that it is straightforward to distinguish between each (or every) probe used in the method.

As discussed above, the pore preferably comprises a vestibule. This is advantageous because the vestibule typically allows the aptamer to enter, but does not allow the aptamer/analyte member complex to enter. This means that the tail can enter the barrel or channel of the pore to differing extents depending on whether or not the aptamer is bound to one of the analyte members. It also means that different regions of the tail are present in the barrel or channel of the pore depending on whether or not the aptamer is bound to one of the analyte members. For a particular pore, it is straightforward to design tails that are suitable for use in the panel of probes. For instance, it is straightforward to design probe tails if the lengths of the vestibule and the barrel or channel of the pore are known.

Each aptamer molecule binds only one of the analyte member molecules in the method of the invention even though it may be capable of binding to more than one analyte member. As discussed above, the entire probe typically moves through the pore along the potential shortly after being contacted with the pore. There is enough time for the aptamer to bind to one analyte member before it moves through the pore. If the probe's target analyte member is not present, the probe moves through the pore without the aptamer binding to an analyte member. If the probe's target analyte is present, the movement of the probe through the pore may be delayed slightly, but is unlikely to be prevented. This is discussed in more detail below.

The tail preferably comprises a polymer. The polymer is capable of entering the pore and affecting the current flowing through the pore. The polymer is preferably a polynucleotide, a polypeptide or a polyethylene glycol (PEG).

The polynucleotide may comprise any of the nucleotides discussed above. However, the polynucleotide in the tail typically comprises nucleotides selected from adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and any of the modified nucleotides discussed above. The polynucleotide preferably comprises nucleotides selected from AMP, TMP, GMP, CMP, UMP, dAMP, dTMP, dGMP or dCMP. The polynucleotide preferably comprises one or more abasic nucleotides. The polynucleotide in the tail may be single stranded or double stranded. The polynucleotide can be a nucleic acid, such as deoxyribonucleic acid (DNA) or ribonucleic acid (RNA). The polynucleotide in the tail can comprise one strand of RNA hybridized to one strand of DNA. The polynucleotide in the tail may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

Typically the tail has an abasic leader sequence, which leader sequence is the first region of the tail to pass into the pore. Preferably the tail comprises at least 2 adjacent abasic residues, for example 3, 4, 5, 6, 7 or more adjacent abasic residues.

Although double stranded polynucleotides in the tail typically cannot pass through the pore, they can be useful in the method of the invention. For instance, the tail may comprise one or more double stranded polynucleotides or polynucleotide regions. The presence of such a double stranded region does not prevent the probe from moving through the pore, but instead simply delays the movement of the probe through the pore as one of the strands in the region is stripped from the probe under the influence of the potential. Such a delay can be seen as the current flowing through the pore is measured. An embodiment in which binding to an analyte delays the movement of the probe through the pore is discussed above. Hence, including one or more double stranded polynucleotide regions in each tail increases the number of possible signals that can be obtained from a population of tails and hence increases the number of analyte members that can be assayed using the method of the invention. A double stranded polynucleotide region may also be used to hold a specific region of the tail, such as a barcode, that is indicative of the probe in the barrel or channel of the pore so that it may be read in accordance with the invention. The one or more double stranded regions may be located on the tail such that they enter the pore before or after the at least two regions that indicate the presence or absence of the analyte member as discussed above. Hence, in a preferred embodiment, the tail comprises a double stranded polynucleotide region and a specific tail region that is indicative of the probe such that the double stranded polynucleotide delays the movement of the probe through the pore and holds the specific tail region in the barrel or channel of the pore. Different specific tail regions between probes (i.e. between different types of probes) typically have different effects on the current flowing through the pore and so can be distinguished from one another. The specific tail region is preferably a polymer. The polymer may be any of those discussed above or below. In such an embodiment, the specific tail region enters the pore and is held in the barrel or channel by the double stranded polynucleotide region. This allows the specific tail region to be identified by its specific effects on the current flowing through the pore. After a short while, one of the strands in the double stranded region is stripped and the probe moves through the pore under the influence of the potential. The binding of the probe to an analyte member may then be measured by (a) a delay in the movement of the probe through the pore and/or (b) the use of at least two specific regions in the tail as discussed above.

The tail preferably comprises at least one single stranded polynucleotide or polynucleotide region. Single stranded polynucleotides are useful in the tail because they can pass through the pore and can easily be divided into different regions that affect the current flowing through the pore in different ways. For instance, different regions of a polynucleotide having different sequences typically affect the current flowing through the pore in different ways. The tail preferably comprises at least two regions of single-stranded polynucleotide with different nucleotide sequences that affect the current flowing through the pore in different ways and one region is situated in the pore when the aptamer is not bound to the one or more analyte members and a different region is situated in the pore when the aptamer is bound to the analyte member. The at least two regions preferably correspond to at least two stretches of different nucleotides. For instance, the polynucleotide may comprise a stretch of adenine nucleotides and a stretch of abasic nucleotides. Each stretch will affect the current flowing through the pore in a different way. Alternatively, the at least two stretches of different nucleotides are different polynucleotide barcodes. Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

The polypeptide in the tail may comprise any amino acids, including any of those discussed above. Different amino acid sequences will affect the current flowing through the pore in different ways and so specific tails may be designed as discussed above for polynucleotides.

Any of the embodiments discussed above for polynucleotides apply to polypeptides (with the substitution of nucleotides with amino acids).

The tail may comprise PEG. PEG will affect the current flowing through the pore in a specific manner. PEG may be used to form one region in the tail that is present in the barrel or channel of the pore when the aptamer is bound or not bound to one of the analyte members. Something other than PEG may be used in the other region in the tail that is present in the barrel or channel of the pore when the aptamer is not bound or bound to the analyte member respectively.

The tail may comprise different combinations of polymers. The tail preferably comprises at least two regions of different polymers that affect the current flowing through the pore in different ways and one region is situated in the pore when the aptamer is not bound to one of the analyte members and a different region is situated in the pore when the aptamer is bound to the analyte member. Table 4 below summarises some preferred combinations.

|   | One region | Different region |
|---|---|---|
| 1 | Polynucleotide | Different polynucleotide |
| 2 | Polypeptide | Different polypeptide |
| 3 | Polynucleotide | Polypeptide |
| 4 | Polypeptide | Polynucleotide |
| 5 | PEG | Polynucleotide |
| 6 | Polynucleotide | PEG |
| 7 | PEG | Polypeptide |
| 8 | Polypeptide | PEG |

The tail may be any length. The tail preferably comprises a polynucleotide from about 7 to about 70 nucleotides in length, such as from about 10 to about 60, from about 20 to about 50 or from about 30 to about 40 nucleotides in length.

The tail may comprise any of the polynucleotides used in the Examples. In particular, the tail preferably comprises residues 1 to 30 of any of SEQ ID NOs: 7 to 23. The panel of probes preferably comprises a population of tails that correspond to residues 1 to 30 of SEQ ID NOs: 7 to 23.

Distinctive Currents

Each probe (i.e. each type of probe) affects the current flowing through the pore in a distinctive manner. In other words, a probe affects the current flowing through the pore in a manner that can be distinguished or differentiated from the way in which a different probe affects the current flowing through the pore. This allows the identity of each probe (i.e. each type of probe) to be measured in accordance with the invention. The binding of the probe to an analyte member can then be measured as discussed above. Since the identity of each probe and the binding of each probe to an analyte member can be measured, the presence or absence of each analyte member can be determined.

Each probe (i.e. each type of probe) preferably affects the current flowing through the pore in a distinctive manner when it binds to one of the analyte members. In other words, the binding of an analyte member to a probe preferably affects the current flowing through the pore in a manner that can be distinguished or differentiated from the way in which a different probe affects the current flowing through the pore when it binds an analyte member. The different probes may bind to the same analyte member.

The distinctive manner may concern the extent to which the current flowing through the pore is affected, i.e. a change in amount of current that flows through the pore as the probe binds, and/or the time for which the current is affected by binding of the probe (the "dwell time"). The value of the current disruption is of greater value than the dwell time as the former provides more distinct signatures, whereas dwell times have broader distribution. The distinctive manner may concern the extent to which the variance of the current flowing the through the pore is affected. The variance may increase or decrease as a result of the binding of an analyte member to a probe. Control experiments may be carried out to ensure that different probes have different effects on the current flowing through the pore when the probe binds to one of the analyte members. Such control experiments can also help to determine the effect a particular probe has on the current flowing through the pore when the probe is bound to the analyte member. Results from carrying out the method of the invention on a test sample can then be compared with those derived from such control experiments in order to determine whether a particular analyte is present or absent in the test sample.

The distinctiveness between probes can be achieved via differences in their lengths. Longer probes will affect the current flowing through a pore for more time, i.e. longer dwell time. Shorter probes will affect the current flowing through the pore for less time, i.e. shorter dwell time.

The distinctiveness between probes can be achieved via differences in their aptamers and/or tails. For instance, different aptamers bind to analytes to different degrees, i.e. have different binding constants. An aptamer that binds more strongly to an analyte member will prevent the probe from moving through the pore for longer and this can be identified by measuring the current flowing through the pore. The opposite is also true, i.e. an aptamer that binds less strongly to an analyte member will prevent the probe from moving through the pore for less time and this can be identified by measuring the current flowing through the pore.

In preferred embodiments discussed above, a specific region of the tail is briefly held in the barrel or channel of the pore when an aptamer binds to one of the analyte members or when a double stranded polynucleotide region in the tail enters the pore. Differences in such specific regions between different probes, such as the presence of different polymers. For example, single stranded and double stranded DNA, or different sequences of the same type of polymer, for example where one sequence is two or more adjacent abasic residues, can also account for the distinctiveness between the probes. It is straightforward to design a panel of probes that have the required distinctiveness.

Each probe (i.e. each type of probe) also preferably affects the current flowing through the pore in a distinctive manner when its aptamer is not bound to one of the analyte members. In other words, in the absence of the analyte member, the probe affects the current flowing through the pore in a manner that can be distinguished or differentiated from the way in which a different probe affects the current flowing through the pore when its analyte member is absent. Different probes may bind to the same analyte member. This "absence" distinctiveness can further add to the ability to distinguish between different probes and thus analytes, especially if different probes bind to the same analyte member, and therefore enhance the multiplex nature of the assay. This preferred distinctiveness can also be determined using control experiments as described above.

This preferred "absence" distinctiveness between probes can be achieved via differences in the probes' length and/or tails. As discussed above, the entire probe moves through the pore in the absence of the analyte member and affects the current flowing through the pore as it does. Different probes (i.e. different types of probes) will affect the current flowing through the pores for different amounts of time, i.e. will have different dwell times. As discussed above, when the aptamer is not bound to an analyte member or a double stranded polynucleotide region enters the pore, a specific region of the tail is briefly held in the barrel or channel of the pore. Differences in such specific regions between different probes, such as the presence of different polymers or different sequences of the same type of polymer, can account for the distinctiveness between the probes. As discussed above, tails can include one or more regions of double stranded polynucleotide. These allow different probes to be distinguished. For example, different tails can comprise different numbers of such regions and/or such regions of different lengths.

Apparatus and Conditions

Electrical measurements may be made using standard single channel recording equipment as describe in Stoddart, D. S., et al., (2009), *Proceedings of the National Academy of Sciences of the United States of America* 106, p 7702-7707, Lieberman K R et al, J Am Chem Soc. 2010; 132(50): 17961-72, and International ApplicationW0-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods involve measuring the current flowing through the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may be carried out on a silicon-based array of wells where each array comprises 128, 256, 512, 1024 or more wells.

The methods of the invention may involve the measuring of a current flowing through the pore. Suitable conditions for measuring ionic currents through transmembrane pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The sample and panel of probes may be contacted with the pore on either side of the membrane. The sample and panel of probes are typically contacted with the pore on the same side of the membrane.

The sample and the panel of probes may be contacted the pore in any order. It is preferred that the sample is contacted with the pore before the panel or at the same time as the panel. If the panel is contacted with the pore before the sample is contacted with the pore, it is essential to ensure that sufficient probes remain available for binding to the analyte members (and have not all crossed the membrane through the pore).

Methods of Measuring Concentration

The method of the invention preferably further comprises, for those probes that bind the one or more analyte members, comparing the different currents flowing through the pore when each probe is bound and unbound. This helps to determine the concentration of the analyte members present in the sample, generally by reference to a calibration curve, use of equilibrium constants or reference to control data. Methods for calculating the concentration are well known in the art.

The invention also provides a method of determining in a sample the concentration of one or more analyte members of a group of two or more analytes, the method comprising:

(i) carrying out a method of the invention as described above; and (ii) for one or more analyte members shown to be present in the sample comparing the current flowing through the pore in step (b) with control or reference data for each analyte member and thereby determining the concentration of the one or more analyte members in the sample. Step (i) preferably comprises, for those probes that bind the one or more analyte members, comparing the different currents flowing through the pore when each probe is bound and unbound. Control or reference data can be generated by conducting control experiments in which known concentrations of an analyte member are used to calibrate the assay. This is described in Example 2.

Panels and Kits

The invention also provides a panel of probes for determining in a sample the presence, concentration or absence of one or more analyte members of a group of two or more analytes. The panel comprises two or more probes, wherein each probe recognises one or more of the analyte members and comprises (i) an aptamer that binds to one or more analyte members and (ii) a tail which is capable of entering a transmembrane pore and has different effects on the current flowing through the pore depending on whether or not the aptamer in the probe is bound to one of the analyte members, wherein each probe affects the current flowing through the pore in a distinctive manner, and wherein each analyte member in the group of two or more analytes is recognised by at least one probe in the panel. Any embodiments discussed above with reference to the method of the invention equally apply to the panel of the invention. Each probe in the panel preferably further comprises a chemical group that allows it to be coupled to a membrane. The chemical group is preferably cholesterol.

The invention also provides a kit for determining in a sample the presence, concentration or absence of one or more analyte members of a group of two or more analytes. The kit comprises (a) a panel of probes of the invention and (b) a transmembrane pore. Any of the embodiments discussed above with reference to the method of the invention equally apply to the kits.

The kit may further comprise the components of a membrane, such as the phospholipids needed to form an amphiphilic layer, such as a lipid bilayer.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for determining in a sample the presence, concentration or absence of one or more analyte members of a group of two or more analytes. The apparatus comprises a plurality of pores and a panel of probes of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the membrane and plurality of pores and being operable to perform analyte member characterisation using the pores;

at least one reservoir for holding material for performing the characterising;

a fluidics system configured to controllably supply material from the at least one reservoir to the sensor device; and a plurality of containers for receiving respective samples, the fluidics system being configured to supply the samples selectively from the containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

The following Examples illustrate the invention.

Example 1

This example illustrates how a nanopore can be used to detect the presence of the protein thrombin.

Materials and Methods

Electrical measurements were acquired using the standard 128 well silicon chips (format 75 µm diameter, 20 µm depth and 250 µm pitch) which were silver plated (WO 2009/077734). Chips were initially washed with 20 mL ethanol, then 20 mL dH$_2$O, then 20 mL ethanol prior to CF4 plasma treatment. The chips used were then pre-treated by dip-coating, vacuum-sealed and stored at 4° C. Prior to use the chips were allowed to warm to room temperature for at least 20 minutes.

Bilayers were formed by passing a series of slugs of 3.6 mg/mL 1,2-diphytanoyl-glycero-3-phosphocholine lipid (DPhPC, Avanti Polar Lipids, Ala., USA) dissolved in 1 M KCl, 10 mM Tris, pH 7.5, at 0.45 µL/s across the chip. Initially a lipid slug (250 µL) was flowed across the chip, followed by a 100 µL slug of air. Two further slugs of 155 µL and 150 µL of lipid solution, each separated by a 100 µL slug of air were then passed over the chip. After bilayer formation the chamber was flushed with 3 mL of buffer at a flow rate of 3 µl/s. Electrical recording of the bilayer formation was carried out at 10 kHz with an integration capacitance of 1.0 pF.

A solution of the biological nanopore was prepared using αHL-(E111N/K147N)₇ (NN) (SEQ ID NO: 2) (Stoddart, D. S., et al., (2009), *Proceedings of the National Academy of Sciences of the United States of America* 106, p 7702-7707) (1 μM diluted 1/80,000) in 1 M KCl, 25 mM Tris pH 7.5. A holding potential of +180 mV was applied and the solution flowed over the chip. Pores were allowed to enter bilayers until 10% occupancy (12 single pores) was achieved. The sampling rate was then reduced to 7 kHz, the potential reduced to zero, and the integration capacitance maintained at 1.0 pF.

A control programme, which cycled through periods of positive holding potential followed by rest periods where no potential was applied, was run for 5 minutes. The control programme applied a potential of 0 mV for 10 seconds, followed by a potential of +170 mV for a further 50 seconds and this cycle was repeated up to 20 times.

After five minutes the script was stopped and 5A15x10A_TBA (SEQ ID NO: 7, 1.25 μM) in 1M KCl, 10 mM Tris pH 7.5 was pipetted into the chamber. The control programme was then run for a total of 15 minutes. Following this, 5A15x10A_TBA (1.25 μM) and thrombin (1 μM) (Cat No. T6884, Sigma-Aldrich, Dorset, UK), which had been pre-incubated together for a minimum of 5 minutes in 1 M KCl, 10 mM Tris pH 7.5, were flowed into the chamber and the control programme run for a further 15 minutes. At the end of the experiment the control programme was stopped.

Discussion

Using the above method it was possible to detect characteristic block levels in the presence and absence of thrombin. Upon the addition of probe 5A15x10A_TBA (SEQ ID NO:7) only a block level at level 1 was observed (see FIG. 2A). Whereas, when probe 5A15x10A_TBA had been pre-incubated with thrombin an additional level (level 2; FIG. 2B) was also detected. Upon binding of thrombin to probe 5A15x10A_TBA a higher than average current flow was measured, indicating that the abasic region (x) was within the β-barrel. The difference between the two levels was 30.5 pA (FIG. 2B). The same experiment was carried out with SEQ ID NOs: 8-18 (8=11x19A_TBA, 9=13x17A_TBA, 10=15x15A_TBA, 11=17x13A_TBA, 12=19x11A_TBA, 13=21x9A_TBA, 14=23x7A_TBA, 15=25x5A_TBA, 16=27x3A_TBA, 17=29x1A_TBA and 18=30x0A_TBA).

Example 2

This example illustrates how a nanopore can be used to detect the concentration of the protein thrombin in solution.
Materials and Methods Electrical measurements were acquired using the standard 128 well silicon chips (format 75 μm diameter, 20 μm depth and 250 um pitch) which were silver plated (WO 2009/077734). In order to carry-out experiments which allowed determination of the concentration of thrombin, the same experimental set-up procedure was performed as described in Example 1 (using the nanopore αHL-(E111N/K147N)₇ (SEQ ID NO: 2) and buffer 1M KCl, 10 mM TRIS pH 7.5), with the same initial control programme (10 seconds at 0 mV, 50 seconds at 170 mV-repeated up to 20 times) run for 5 minutes.

After five minutes the script was stopped and 5A15x10A_TBA (1.25 μM) in 1M KCl, 10 mM Tris pH 7.5 was pipetted into the chamber. The control programme was then run for a total of 15 minutes. Following this, 5A15x10A_TBA (SEQ ID NO: 7, 1.25 μM) and thrombin (100 nM) (Cat No. T6884, Sigma-Aldrich, Dorset, UK) which had been pre-incubated together for at least 5 minutes in 1 M KCl, 10 mM Tris pH 7.5 were flowed into the chamber and the control programme run for a further 15 minutes. The entire solution volume above the chip was then replaced with a solution of 5A15x10A_TBA (1.25 μM) and thrombin (250 nM) which had been pre-incubated for a minimum of 5 minutes in 1 M KCl, 10 mM Tris pH 7.5 and the control programme run for a further 15 minutes. This process was repeated for 500 nM, 750 nM and 1250 nM concentrations of thrombin. At the end of the experiment the control programme was stopped.

Discussion

Figure 3A:
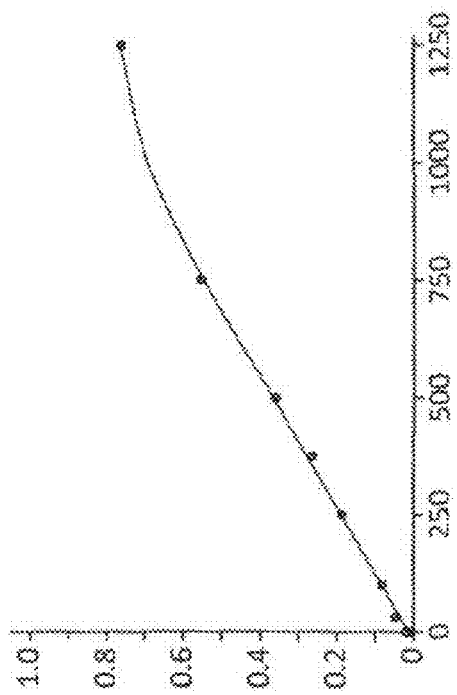

Using the above method it was possible to measure the frequency of the events which corresponded to thrombin bound to probe 5A15x10A_TBA (SEQ ID NO: 7) (see FIGS. 2A-2B). This data was then used to produce calibration plots of the concentration of thrombin vs. the ratio of the thrombin bound events when compared to the total number of blocking events (bound and unbound combined), see FIGS. 3A-3B. These calibration plots can then be used to determine the concentration of an unknown sample of thrombin.

Example 3

This example illustrates how a nanopore can be used to detect the presence of the protein thrombin utilising a significantly lower concentration of thrombin binding probe.
Materials and Methods Electrical measurements were acquired using the standard 128 well silicon chips (format 75 μm diameter, 20 μm depth and 250 um pitch) which were silver plated (WO 2009/077734). In order to carry-out experiments which allowed detection of thrombin using a much lower concentration of cholesterol-tagged probe (SEQ ID NO: 19 which has a cholesterol TEG at the 3' end), the same experimental set-up procedure was performed as described in Example 1 (using the nanopore αHL-(E111N/K147N)₇ (NN) (SEQ ID NO: 2) and the buffer 1M KCl, 10 mM Tris pH 7.5), with the initial control programme (10 seconds at 0 mV, 50 seconds at 170 mV—repeated up to 20 times) run for 5 minutes.

The same procedure steps were followed as in Example 1 except that a different aptamer at a lower concentration was used (aptamer only run=15x15A_TBA_3'CholTEG (100 pM) in 1 M KCl, 10 mM Tris pH 7.5 and aptamer plus thrombin run=15x15A_TBA_3'CholTEG (100 pM) and thrombin (100 nM) (Cat No. T6884, Sigma-Aldrich, Dorset, UK)).

Discussion

Using the above method it was possible to detect characteristic block levels in the presence and absence of thrombin using a significantly lower concentration of probe 15x15A_TBA_3'CholTEG (SEQ ID NO: 19 which has a cholesterol TEG at the 3' end). In the above example it was possible to observe level 1 using probe 15x15A_TBA_3'CholTEG and levels 1 and 2 when probe 15x15A_TBA_3'CholTEG was pre-incubated with thrombin (FIGS. 4A-4B). The step level change was observed using only a 100 pM concentration of the cholesterol-tagged probe 15x15A_TBA_3'CholTEG. This concentration is over a magnitude lower than was tested in Example 2.

Example 4

This example illustrates how a nanopore can be used to detect the presence of the protein thrombin utilising a number of different thrombin binding probes which each produce their own distinctive step level signal.

Materials and Methods

Electrical measurements were acquired using the standard 128 well silicon chips (format 75 µm diameter, 20 µm depth and 250 um pitch) which were silver plated (WO 2009/077734). In order to carry-out experiments which allowed detection of thrombin using a variety of different probes, the same experimental set-up procedure was performed as described in Example 1 (using the nanopore αHL-(E111N/K147N)$_7$ (NN) (SEQ ID NO: 2) and the buffer 1 M KCl, 10 mM Tris pH 7.5), with the same initial control programme (10 seconds at 0 mV, 50 seconds at 170 mV—repeated up to 20 times) run for 5 minutes.

After five minutes the script was stopped and the probes 5A15x10A_TBA (SEQ ID NO: 7, 310 nM), 19x11A_TBA (SEQ ID NO: 12, 310 nM), 17x13A_TBA (SEQ ID NO: 11, 310 nM) and 15x15A_TBA (SEQ ID NO: 10, 310 nM) in 1 M KCl, 10 mM Tris pH 7.5 were pipetted into the chamber. The control programme was then run for a total of 20 minutes. Following this, analytes 5A15x10A_TBA (310 nM), 19x11A_TBA (310 nM), 17x13A_TBA (310 nM) and 15x15A_TBA (310 nM) and thrombin (1.25 µM) (Cat No. T6884, Sigma-Aldrich, Dorset, UK) which had been pre-incubated altogether for a minimum of 5 minutes in 1M KCl, 10 mM Tris pH 7.5 were flowed into the chamber and the control programme run for a further 20 minutes. At the end of the experiment the control programme was stopped.

Discussion

Figure 5A:
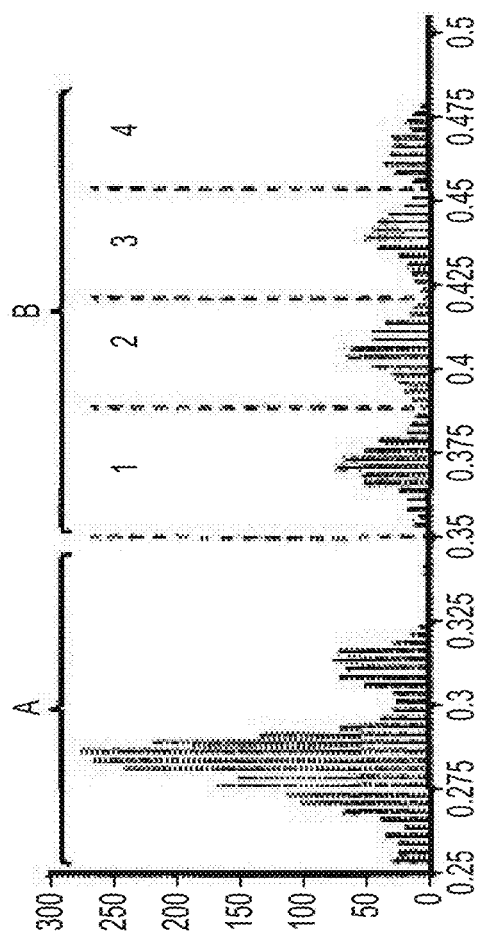
FIGS. 5A-5B illustrate how a number of different aptamers can be used to detect the presence of thrombin, where each aptamer produces its own distinctive step level signal.
Figure 5B:
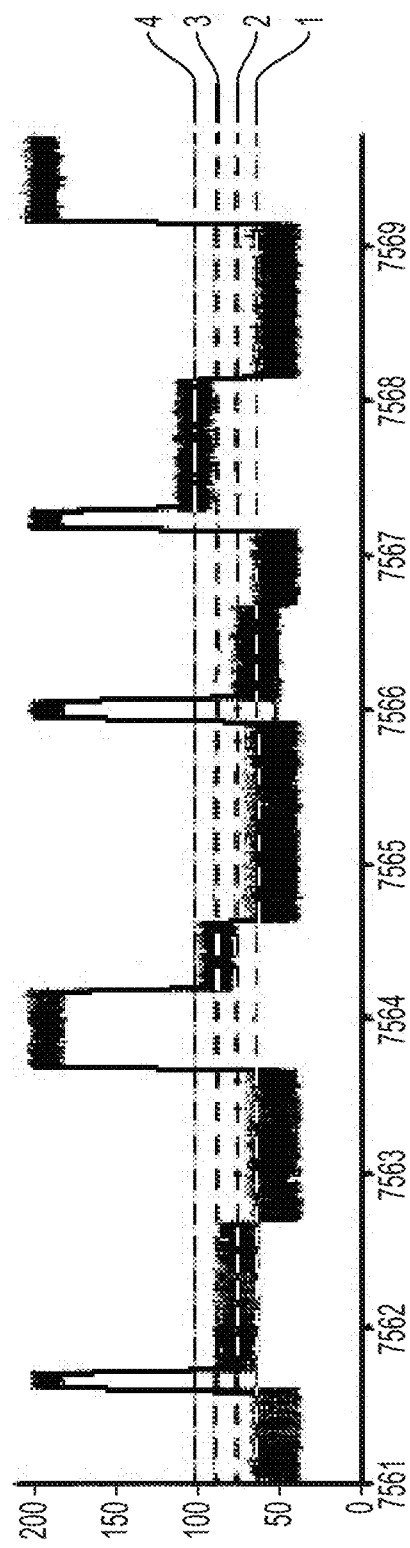

Using the above method it was possible to detect a distinct step level for each of the probes used in both the presence and absence of thrombin (FIGS. 5A and 5B). This experiment shows that the step level observed is specific to the probe tail sequence and, therefore, multiple probe tails could be used to detect more than one protein

Example 5

This example illustrates how a nanopore can be used to detect platelet derived growth factor (PDGF) in solution.

Materials and Methods

Electrical measurements were acquired from single αHL-(E111N/K147N)$_7$ (NN) (SEQ ID NO: 2) nanopores inserted in 1,2-diphytanoyl-glycero-3-phosphocholine lipid (Avanti Polar Lipids) bilayers. Bilayers were formed across 100 µm diameter apertures in 20 µm thick PTFE films (in custom Delrin chambers) via the Montal-Mueller technique, separating two 1 mL buffered solutions (1M KCl, 10 mM Tris pH 7.5). Single-channel currents were measured on Axopatch 200B amplifiers (Molecular Devices) equipped with 1440A digitizers. Ag/AgCl electrodes were connected to the buffered solutions so that the cis compartment (to which both nanopore, probe and PDGF were added) was connected to the ground of the Axopatch headstage, and the trans compartment was connected to the active electrode of the headstage.

After achieving a single pore in the bilayer, a control, at an applied potential of +180 mV, was run for 5 minutes. The script was then stopped and probe 17x8A_PDGF (SEQ ID NO: 20, 0.5 µM) in 1M KCl, 10 mM Tris pH 7.5 buffer was added to the cis compartment of the electrophysiology chamber and the experiment run for 20 minutes. Where long block events (>15 s) were detected, the potential was flipped to −180 mV to manually eject the blocking analyte. The script was then stopped and probe 17x8A_PDGF (0.5 µM) and PDGF (1 µM) (Biorbyt, Cat No: orb80544, Cambridge, UK) which had been pre-incubated together for a minimum of 5 minutes in 1 M KCl, 10 mM Tris pH 7.5 buffer were then added to the cis compartment and the experiment run for a further 20 minutes. Long blocking events were again removed by flipping the applied potential. At the end of the experiment the control programme was stopped.

Discussion

Figure 6A:
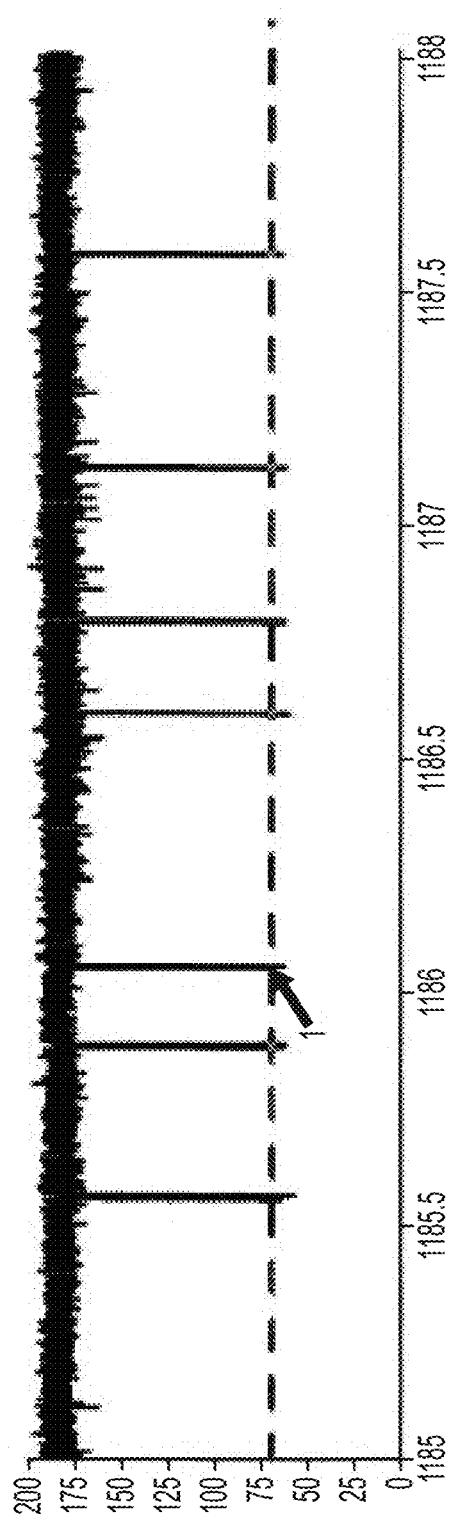
FIGS. 6A-6B illustrate the different block levels that are observed for aptamer sequence 17x8A_PDGF in the presence (FIG. 6B) and absence (FIG. 6A) of PDGF (the y-axis=current (pA) and the x-axis=time (s) for FIGS. 6A and 6B).
Figure 6B:
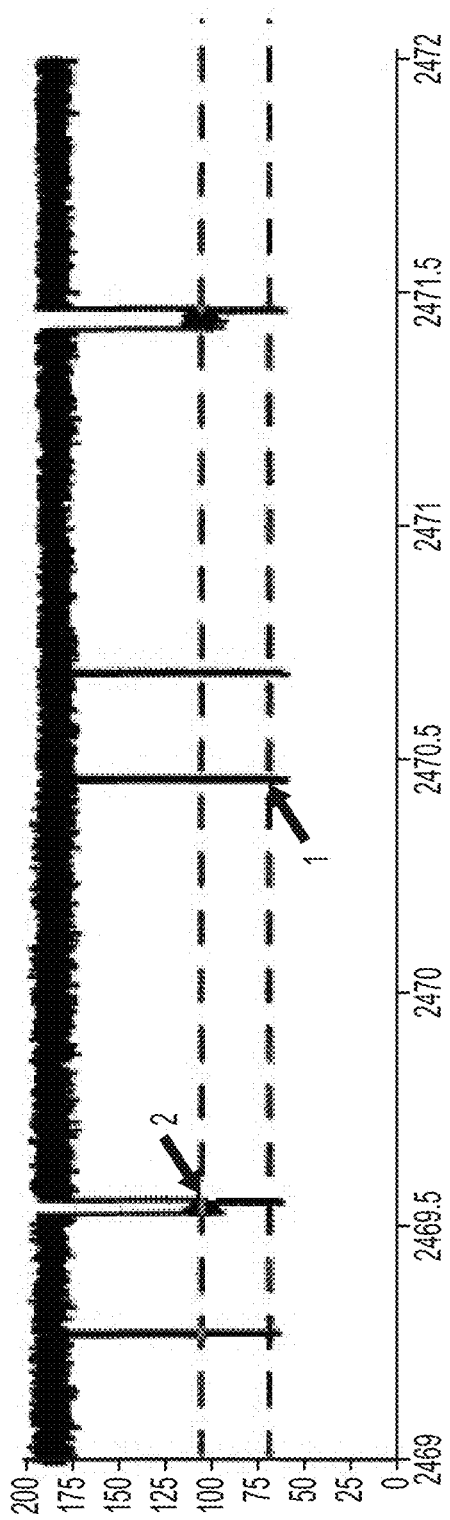
Figure 7A:
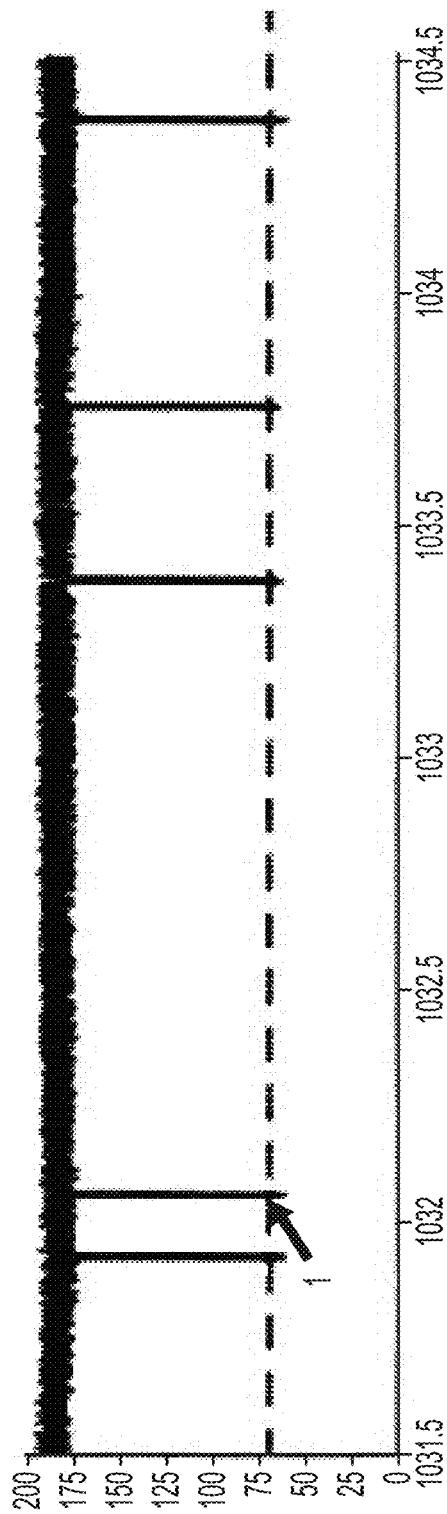
FIGS. 7A-7B illustrate the different block levels that are observed for aptamer sequence 25x_PDGF in the presence (FIG. 7B) and absence (FIG. 7A) of PDGF (the y-axis=current (pA) and the x-axis=time (s) for FIGS. 7A and 7B).
Figure 7B:
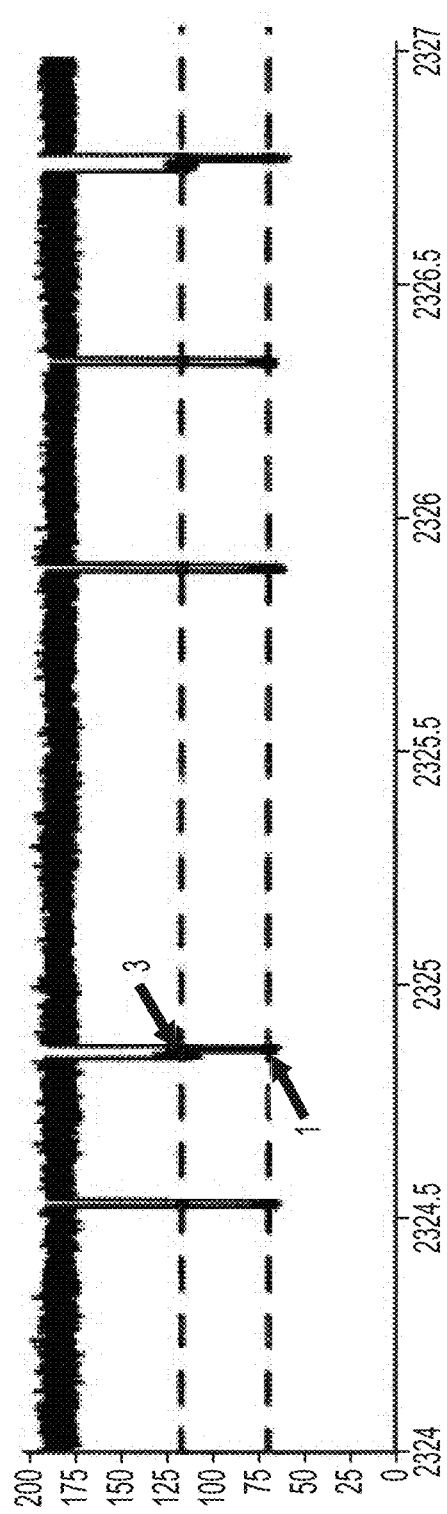

Using the above method it was possible to detect characteristic step levels in the presence and absence of PDGF. By employing probe 17x8A_PDGF (SEQ ID NO: 20) a block level at level 1 was observed (see FIG. 6A). Whereas, when PDGF pre-incubated with 17x8A_PDGF was added to the experimental solution (level 2) was also detected (see FIG. 6B). FIGS. 7A and 7B show the step levels produced in the presence and absence of PDGF when another probe, 25x_PDGF (SEQ ID NO: 21), was used.

Example 6

This example illustrates how a nanopore can be used to detect the concentration of PDGF in solution.

Materials and Methods

Electrical measurements were acquired using the standard 128 well silicon chips (format 75 µm diameter, 20 µm depth and 250 um pitch) which were silver plated (WO 2009/077734). In order to carry-out experiments which allowed determination of the concentration of PDGF, the experimental set-up procedure was performed as described in Example 1 (using the nanopore αHL-(E111N/K147N)$_7$ (NN) (SEQ ID NO: 2) and buffer 1 M KCl, 10 mM Tris pH 7.5), with the same initial control programme (10 seconds at 0 mV, 50 seconds at 170 mV—repeated up to 20 times) run for 5 minutes.

After five minutes the script was stopped and 25x_PDGF (SEQ ID NO: 21, 0.5 µM) in 1M KCl, 10 mM Tris pH 7.5 was pipetted into the chamber. The control programme was then run for a total of 10 minutes. Following this, 25x_PDGF (0.5 µM) and PDGF (10 nM) (Biorbyt, Cat No: orb80544, Cambridge, UK) which had been pre-incubated together for a minimum of 5 minutes in 1M KCl, 10 mM Tris pH 7.5 were flowed into the chamber and the control programme run for 10 minutes. The entire solution volume above the chip was then replaced with a solution of 25x_PDGF (0.5 µM) and PDGF (33 nM) which had been pre-incubated together for a minimum of 5 minutes in 1 M KCl, 10 mM Tris pH 7.5 and the control programme run for a further 10 minutes. This process was repeated for 100 nM, 330 nM and 1 µM concentrations of PDGF. At the end of the experiment the control programme was stopped.

Discussion

Figure 8:
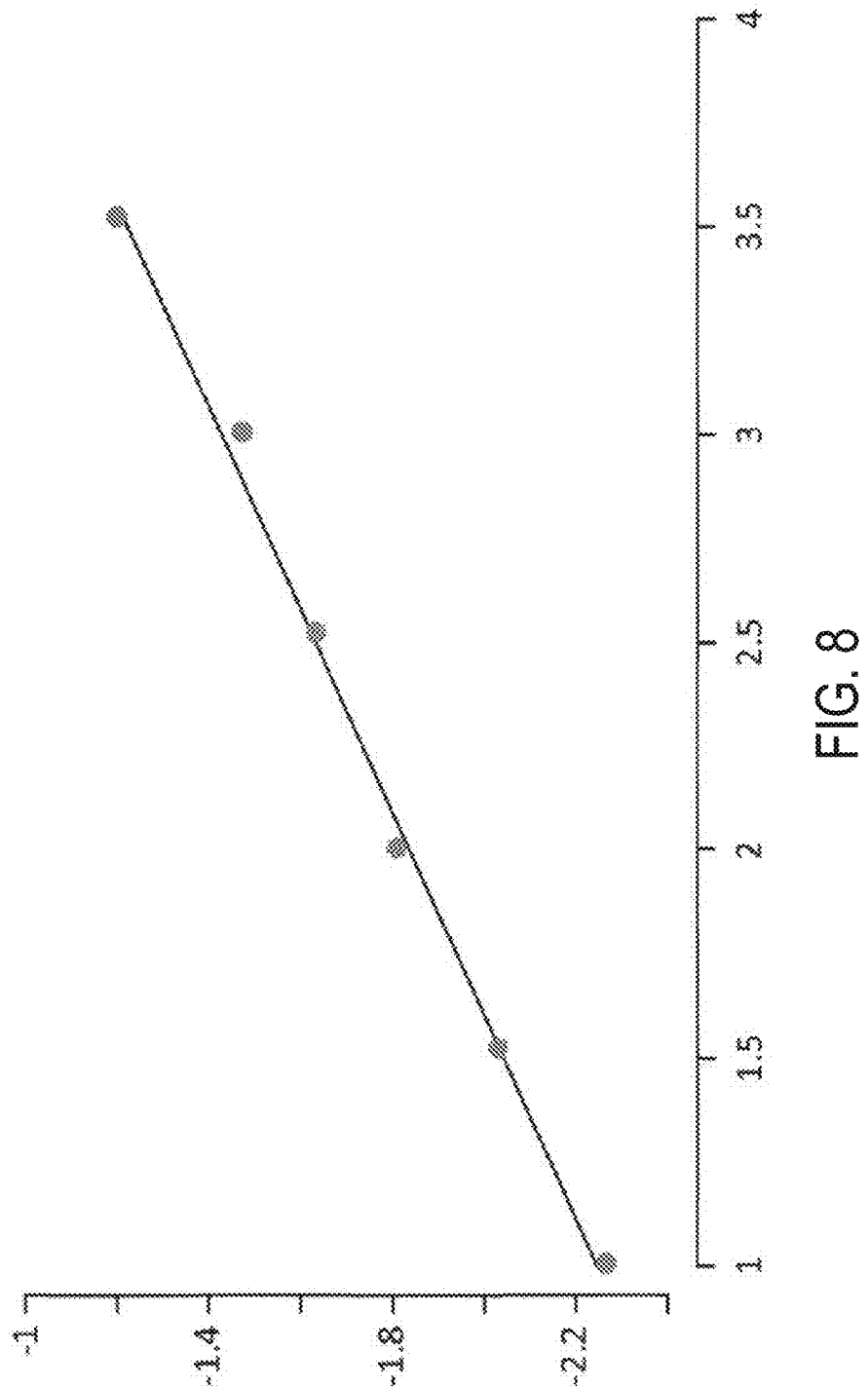
FIG. 8 illustrates the relationship between the PDGF concentration and the observed event ratio (PDGF bound events only compared to PDFG bound and unbound events combined). This graph (y-axis=$\log_{10}$ event rate, x-axis=$\log_{10}$ PDGF concentration (nM)) shows how the ratio between the PDGF bound events and the total number of events (PDGF bound and unbound events) vary with the concentration of PDGF. The probe sequence used in this experiment was 25x_PDGF. Using this calibration graph it is possible to determine the concentration of PDGF in a sample.

Using the above method it was possible to measure the frequency of the events which corresponded to PDGF bound to probe 25x_PDGF (SEQ ID NO: 21, see FIGS. 7A and 7B). This data was then used to produce a calibration plot of concentration of PDGF vs. the ratio of the PDGF bound only events when compared to the total number of blocking events (PDGF bound and unbound combined), see FIG. 8.

This calibration plot can then be used to determine the concentration of an unknown sample of PDGF.

Example 7

This example illustrates how a protein nanopore can be used to detect the presence of ATP in a solution.
Materials and Methods Electrical experiments were set up as described in Example 5 in order to achieve a single pore (using nanopore αHL-(E111N/K147N)$_7$ (NN) (SEQ ID NO: 2) and buffer 1 M KCl, 10 mM Tris pH 7.5) inserted into a lipid bilayer, then a control, at an applied potential of +180 mV, was run for 5 minutes. The same procedure steps were followed as in Example 5 except that a different aptamer, for detecting ATP instead of PDGF, was used. For the aptamer only run the aptamer used in this example was 25x_ATP (SEQ ID NO: 22, 0.5 µM) in 1M KCl, 10 mM Tris pH 7.5 and for the aptamer plus ATP run the following concentrations of reagent were used 25x_ATP (SEQ ID NO: 22, 0.5 µM) and ATP (10 mM) (Cat No: A6559, Sigma-Aldrich, Dorset, UK).

Discussion

Figure 9A:
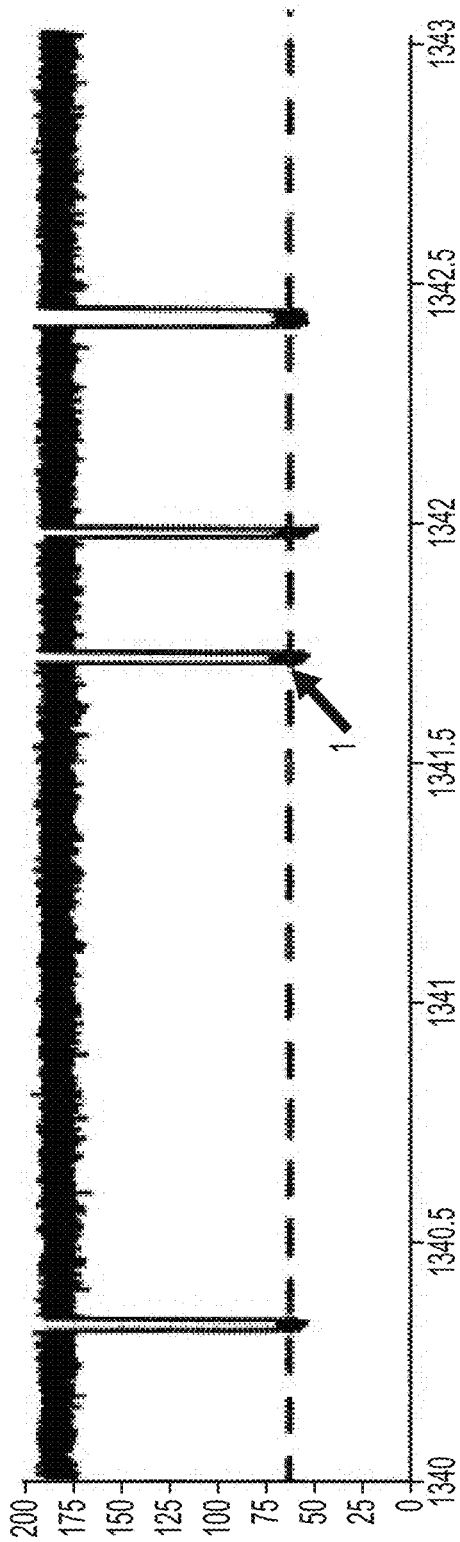
FIGS. 9A-9B illustrate the different block levels that are observed for aptamer sequence 25x_ATP in the presence (FIG. 9B) and absence (FIG. 9A) of ATP (the y-axis=current (pA) and the x-axis=time (s) for FIGS. 9A and 9B).
Figure 9B:
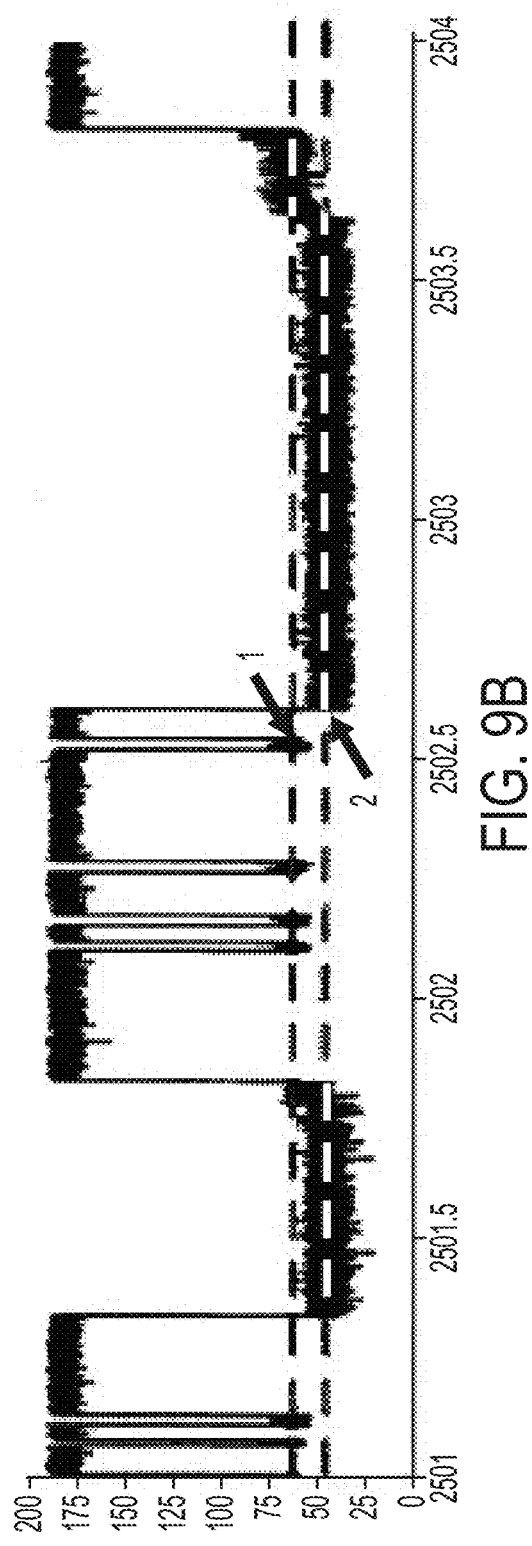
Figure 10A:
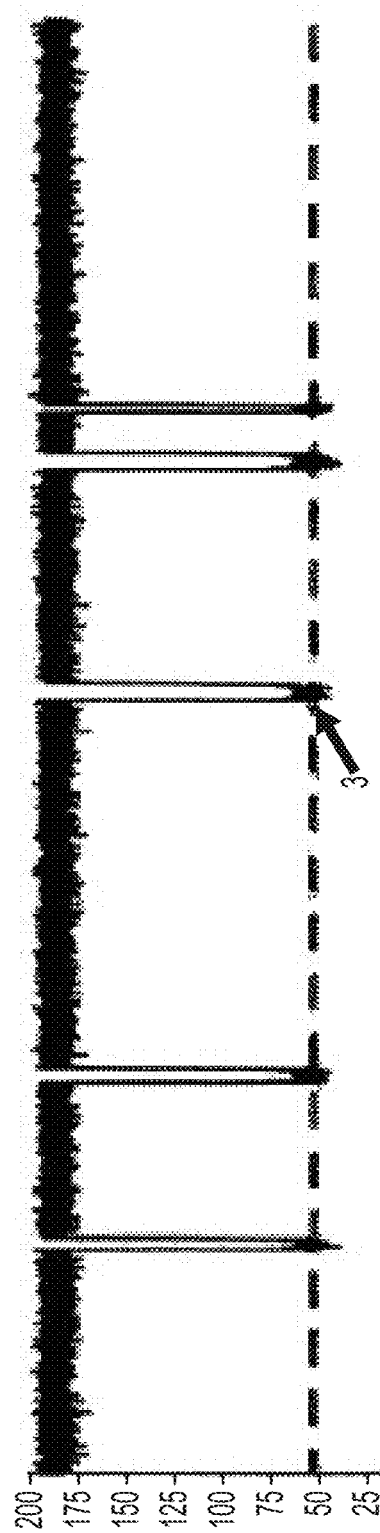
FIGS. 10A-10B illustrate the different block levels that are observed for the aptamer sequence and 17x8A_ATP in the presence (FIG. 10B) and absence (FIG. 10A) of ATP (the y-axis=current (pA) and the x-axis=time (s) for FIGS. 10A and 10B).
Figure 10B:
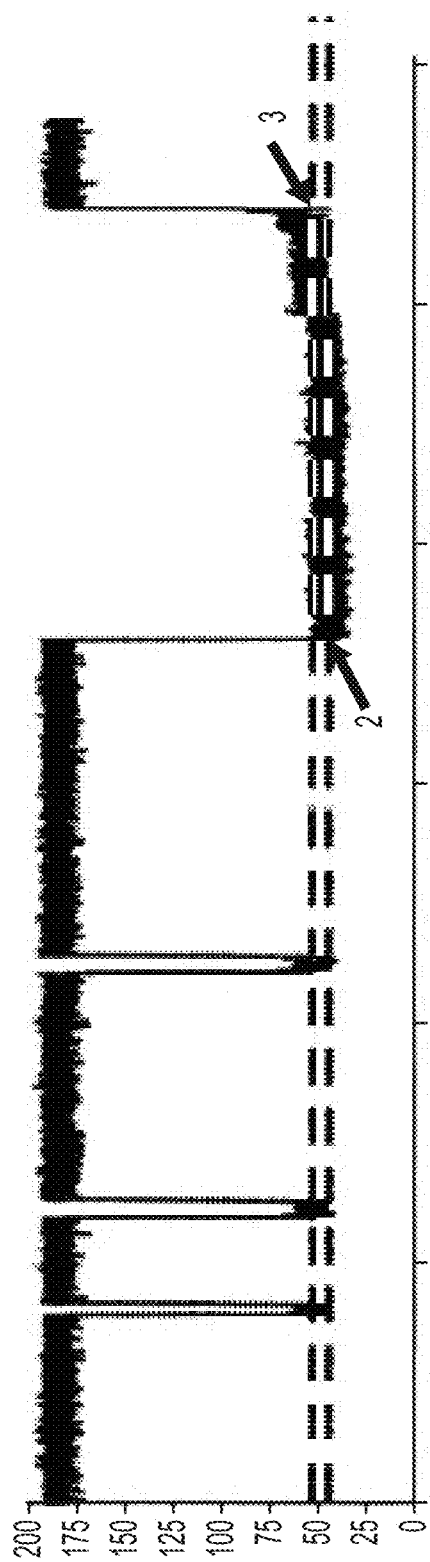

Using the above method it was possible to detect characteristic block levels in the presence and absence of ATP. By employing probe 25x_ATP (SEQ ID NO: 22) a block at level 1 was observed (see FIG. 9A). Whereas, when probe 25x_ATP had been pre-incubated with ATP an additional level (level 2; FIG. 9B) was also detected. In the case of ATP, the event produced by the probe translocating is very short, with the event corresponding to bound ATP being significantly longer (FIG. 9B). FIGS. 10A and 10B show the step levels produced in the presence and absence of ATP when probe 17x8A_ATP (SEQ ID NO: 23) was used.

Example 8

This example illustrates how a protein nanopore can be used to detect the concentration of ATP in solution.
Materials and Methods Electrical experiments were set up as described in Example 5 in order to achieve a single pore (using nanopore αHL-(E111N/K147N)$_7$ (NN) (SEQ ID NO: 2) and buffer 1 M KCl, 10 mM Tris pH 7.5) inserted into a lipid bilayer, then a control, at an applied potential of +180 mV, was run for 5 minutes. The script was then stopped and probe 17x8A_ATP (SEQ ID NO: 23, 0.504) in 1M KCl, 10 mM TRIS pH 7.5 buffer was added to the cis compartment of the electrophysiology chamber and the experiment run for 20 minutes. Where long block events (>15 s) were detected, the potential was flipped to −180 mV to manually eject the blocking analyte. The script was then stopped and probe 17x8A_ATP (0.5 µM) and ATP (1 µM) (Cat No: A6559, Sigma-Aldrich, Dorset, UK) which had been pre-incubated together for a minimum of 5 minutes in 1M KCl, 10 mM TRIS pH 7.5 buffer were then added to the cis compartment and the experiment run for a further 10 minutes. This process was repeated for 3.3 µM, 10 µM and 100 µM concentrations of ATP. At the end of the experiment the control programme was stopped.

Discussion

Figure 11:
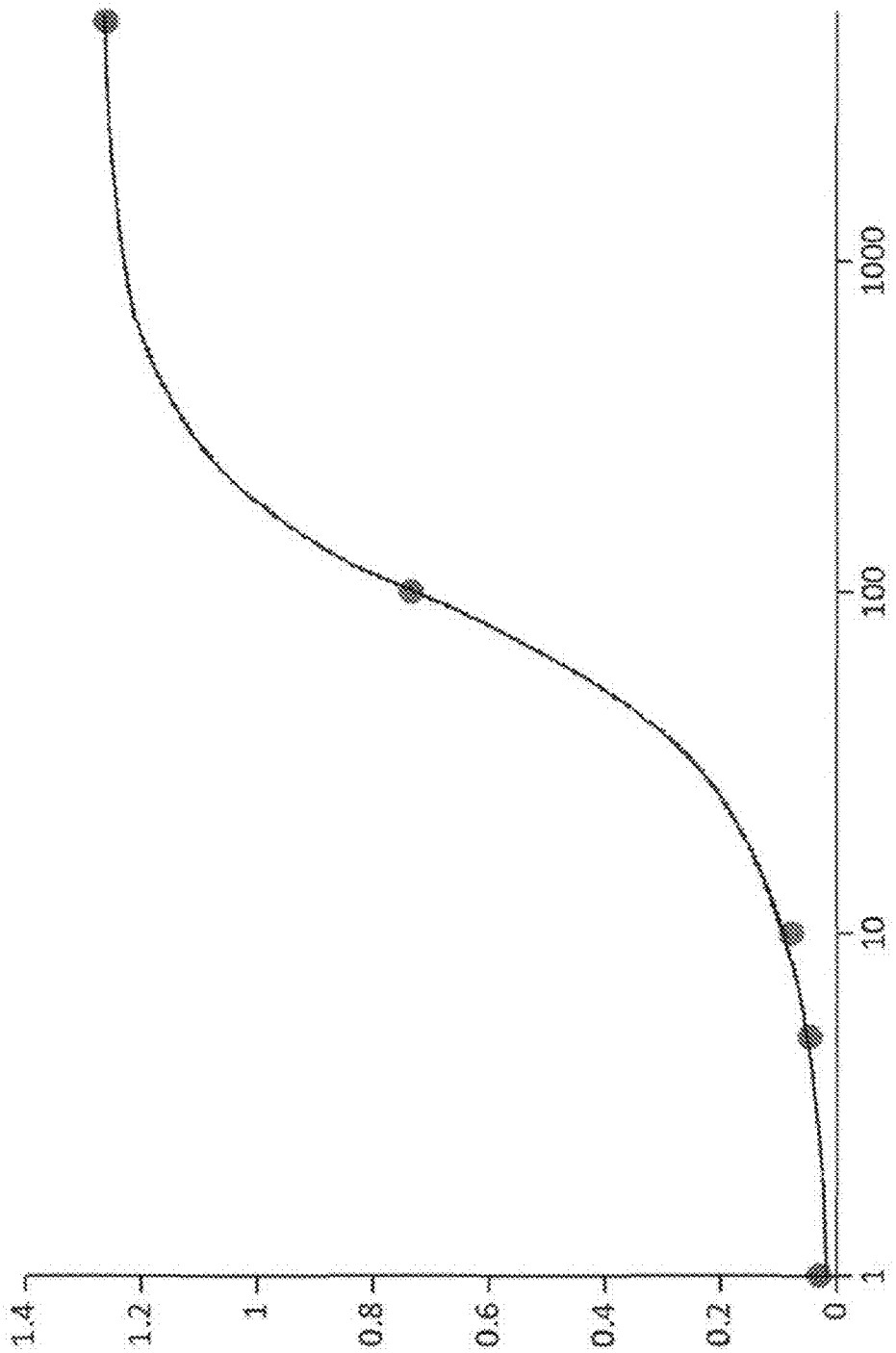
FIG. 11 illustrates the relationship between the ATP concentration and the observed event ratio (ATP bound events only compared to ATP bound and unbound events combined). This graph (y-axis=event rate, x-axis=$\log_{10}$ ATP concentration (μM)) shows how the ratio between the ATP bound events and the total number of events (ATP bound and unbound events), varies with the concentration of ATP. The probe sequence used in this experiment was 17x8A_ATP. Using this calibration graph it is possible to determine the concentration of ATP in a sample. Using aptamer 17x8A_ATP, a similar increase in event rate was observed, as the concentration of ATP increased, as was observed previously for increasing thrombin concentration. However, the Kd of ATP is in the micromolar range so a higher concentration of ATP is needed to obtain a similar event rate.

Using the above method it was possible to measure the frequency of the events which corresponded to ATP bound to probe 17x8A_ATP (SEQ ID NO: 23, see FIGS. 10A and 10B). This data was then used to produce a calibration plot of concentration of ATP vs the ratio of the ATP bound events when compared to the total number of blocking events (ATP bound and unbound combined), see FIG. 11. This calibration plot can then be used to determine the concentration of an unknown sample of ATP. A similar event rate increase was observed for ATP as thrombin, except it was necessary to add a higher concentration of ATP as it has a Kd value in the micromolar range (FIG. 11).

Example 9

This example illustrates how a nanopore can be used to detect the presence of more than one analyte (e.g. ATP, PDFG and thrombin) in solution.
Materials and Methods Electrical experiments were set up as described in Example 5 in order to achieve a single pore (using nanopore αHL-(E111N/K147N)$_7$ (NN) (SEQ ID NO: 2) and buffer 1M KCl, 25 mM Tris pH 7.5) inserted into a lipid bilayer, then the control programme (10 seconds at 0 mV, 50 seconds at +180 mV—repeated up to 20 times) was run for 5 minutes. The script was then stopped and probes 15x15A_TBA (SEQ ID NO: 10, 166 nM), 17x8A_PDGF (SEQ ID NO: 20, 166 nM) and 17x8A_ATP (SEQ ID NO: 23, 166 nM) in 1M KCl, 25 mM TRIS pH 7.5 buffer were added to the cis compartment of the electrophysiology chamber and the control programme run for 10 minutes. ATP (10 mM) (Cat No: A6559, Sigma-Aldrich, Dorset, UK) was then added to the cis compartment and the control programme run for a further 10 minutes. This process was repeated for 1 µM, PDGF (Biorbyt, Cat No: orb80544, Cambridge, UK) and 0.5 µM thrombin (Cat No. T6884, Sigma-Aldrich, Dorset, UK). At the end of the experiment the control programme was stopped.

Discussion

Using the above method it was possible to detect characteristic step level changes for all three analytes when present in solution. All three step signals, that had been observed for each of the analytes when tested individually, could be noted in the above experiment (see FIGS. 12A and 12B). ATP and PDGF both produce shorter binding events than thrombin, this is likely to be owing to the lack of quadruplex structure with these analytes. Therefore, using this method it would be possible to detect any of the three analytes in an unknown mixture.

Example 10

This example illustrates how it is possible to compare the experimental event ratio, that was determined for a number of concentrations of thrombin, with that of theoretically calculated event ratios.
Materials and Methods—Experimental Data Acquisition Electrical experiments were set up as described in Example 5 in order to achieve a single pore (using nanopore αHL-(E111N/K147N)$_7$ (NN) (SEQ ID NO: 2) and buffer 1 M KCl, 10 mM Tris pH 7.5) inserted into a lipid bilayer, then the control programme (10 seconds at 0 mV, 50 seconds at +180 mV—repeated up to 20 times) was run for 5 minutes. Following this, 5A15x10A_TBA (SEQ ID NO: 7, 1.25 µM) and thrombin (10 nM) (Cat No. T6884, Sigma-Aldrich, Dorset, UK) which had been pre-incubated together for at least 5 minutes in 1M KCl, 10 mM Tris pH 7.5 were flowed into the chamber and the control programme run for a further 15 minutes. The entire solution volume above the chip was then replaced with a solution of 5A 15x10A_TBA (1.25 µM) and thrombin (33 nM) which had been pre-incubated for a minimum of 5 minutes in 1 M KCl, 10 mM Tris pH 7.5 and the control programme run for a further 15 minutes. This process was repeated for 100 nM, 330 nM and 1000 nM concentrations of thrombin. At the end of the experiment the control programme was stopped.

Theoretical Calculation

The dissociation constant can be calculated using the following equation:—

$$K_d = \frac{[P][L]}{[C]}$$

where [P]=molar equilibrium concentration of the protein, [L]=molar equilibrium concentration of the aptamer and [C]=molar equilibrium concentration of the protein-aptamer complex.

The $K_d$ for the binding of thrombin to its aptamer is known to be 50 nM. The values of the starting concentrations of P and L are known and these can be used to calculate the molar equilibrium concentrations by solving the below equation (where x=number of moles of protein-aptamer complex).

$$K_d = \frac{([P_{start}] - x) \cdot ([L_{start}] - x)}{x}$$

Figure 13:
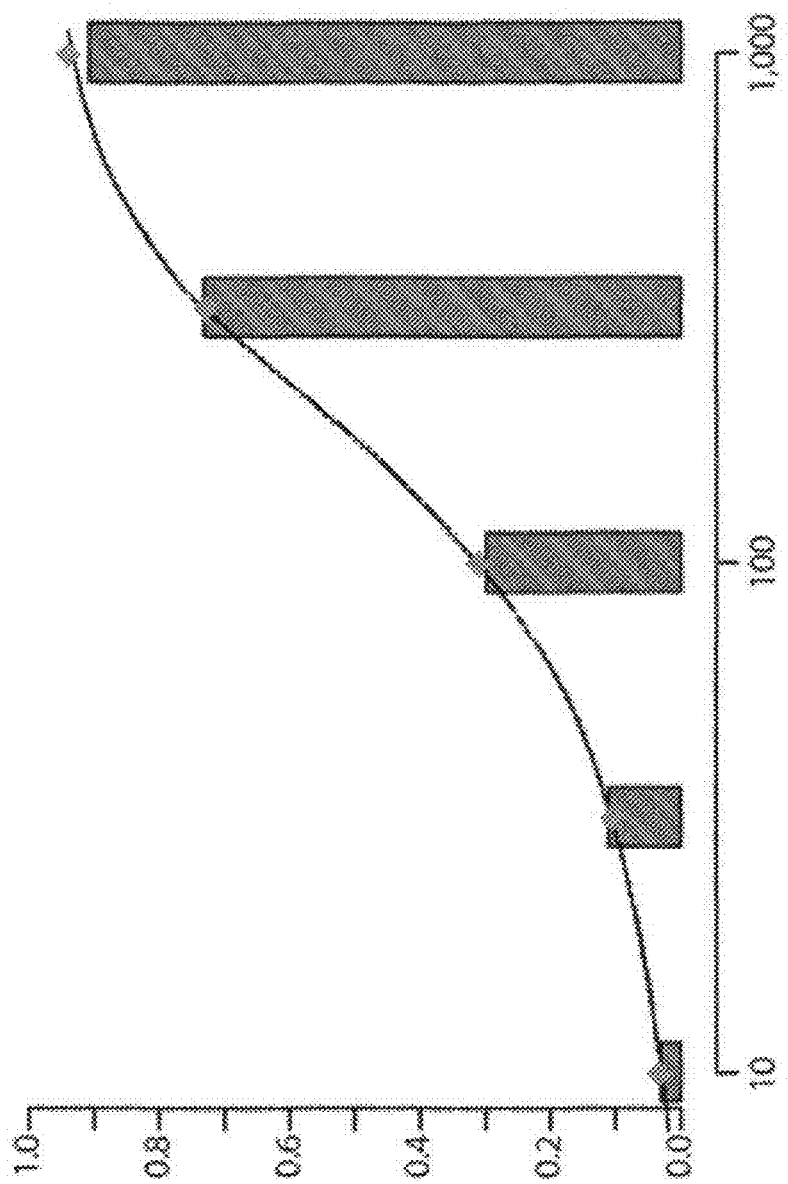
FIG. 13 shows a calibration plot (event ratio (y-axis) against thrombin concentration (nM) (x-axis)) of the theoretically calculated (shown as a black line) and experimentally observed values (shown as a grey bar chart). It is clear from the graph that the theoretical value closely matches that which was determined experimentally.

The above quadratic equation can be rearranged and solved (to determine the value of x) for a number of starting concentrations of P and L. These values can then be plotted to give a theoretical calibration plot of the event ratio against thrombin concentration. The calibration plot in FIG. 13 shows theoretically calculated values (shown as a black line) and experimentally observed values (shown as a grey bar chart). It is clear from the graph that the theoretical value closely matches that which was determined experimentally.

Example 11

This example illustrates how a nanopore can be used to detect the presence of the protein streptavidin.

Materials and Methods

Electrical measurements were acquired using the standard 128 well silicon chips (format 75 µm diameter, 20 µm depth and 250 um pitch) which have platinum electrodes in each well structure. In order to carry-out experiments which allowed detection of streptavidin using a probe, the same experimental set-up procedure was performed as described in Example 1 (using nanopore αHL-(E111N/K147N)$_7$ (NN) (SEQ ID NO: 2) and buffer 625 mM NaCl, 100 mM HEPES, 75 mM potassium ferrocyanide, 25 mM potassium ferricyanide, pH 8.0), with the same initial control programme (10 seconds at 0 mV, 50 seconds at 170 mV—repeated up to 20 times) run for 5 minutes.

The same procedure steps were followed as in Example 1 except that a different aptamer was used (aptamer only run=Strep probe 1 (SEQ ID NO: 24, 1.0 µM) in 625 nm NaCl, 100 mM HEPES, 75 mM potassium ferrocyanide, 25 mM potassium ferricyanide, pH 8.0 and aptamer plus streptavidin run=strep probe 1 (SEQ ID NO: 24, 1.0 µM) and streptavidin (5.0 nM) (Sigma Aldrich)).

Discussion

Figure 14A:
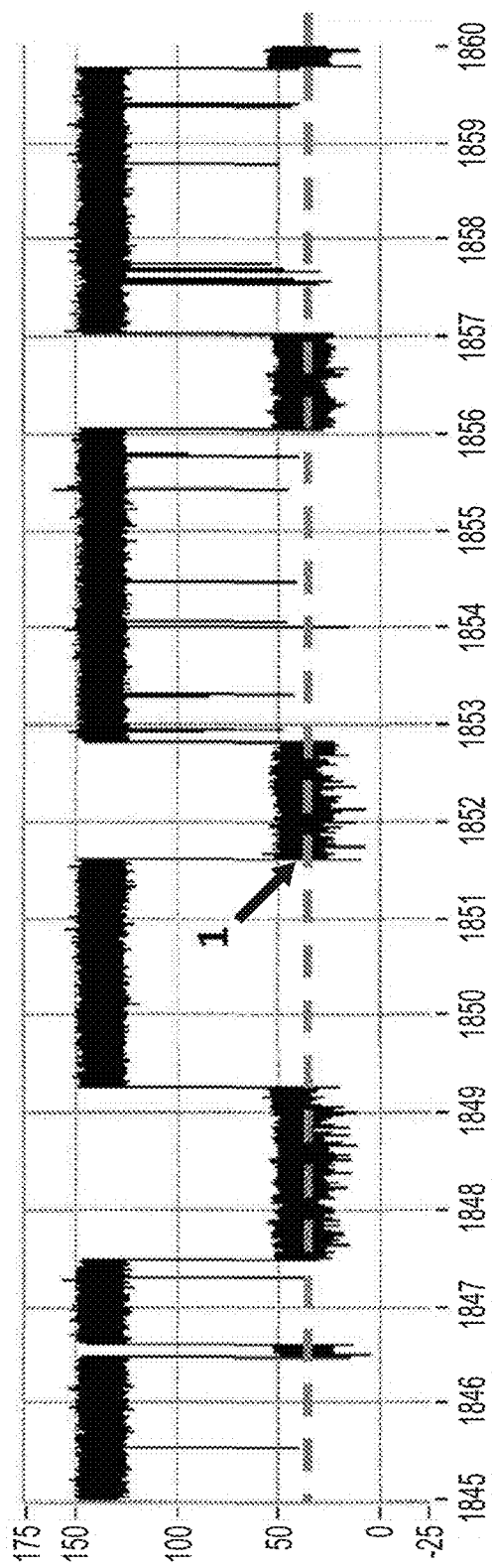
FIGS. 14A-14B illustrate the different block levels that are observed for aptamer sequence strep probe 1 (SEQ ID NO: 24) in the presence (FIG. 14B) and absence (FIG. 14A) of streptavidin (the y-axis=current (pA) and the x-axis=time (s) for FIGS. 14A and 14B).
Figure 14B:
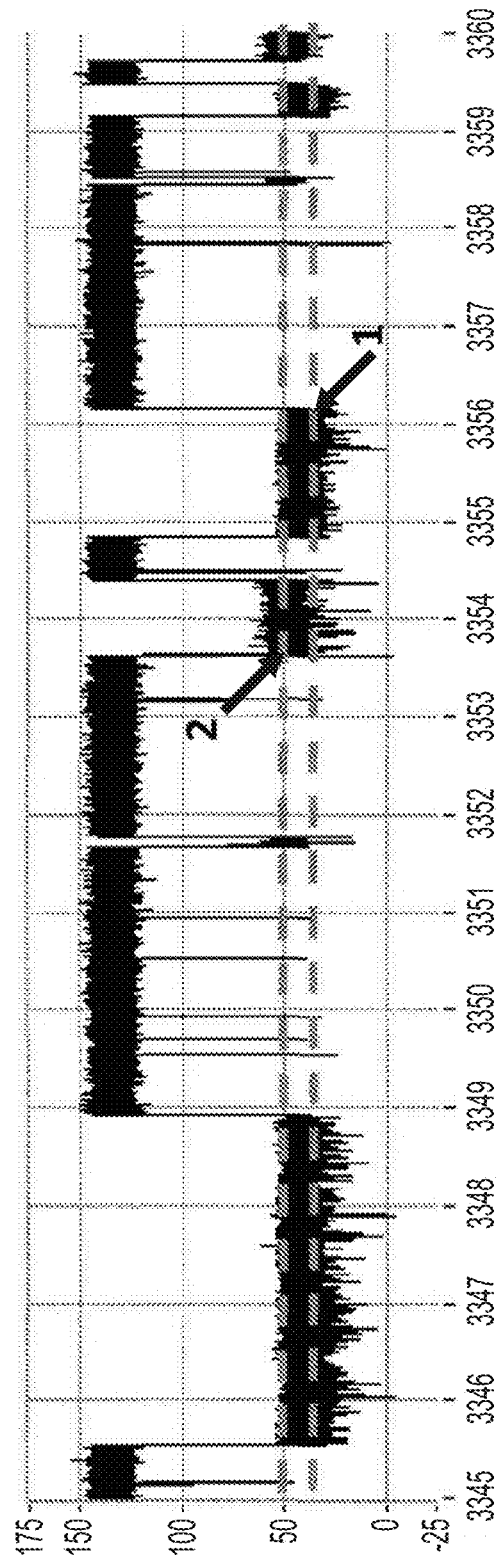
Figure 15:
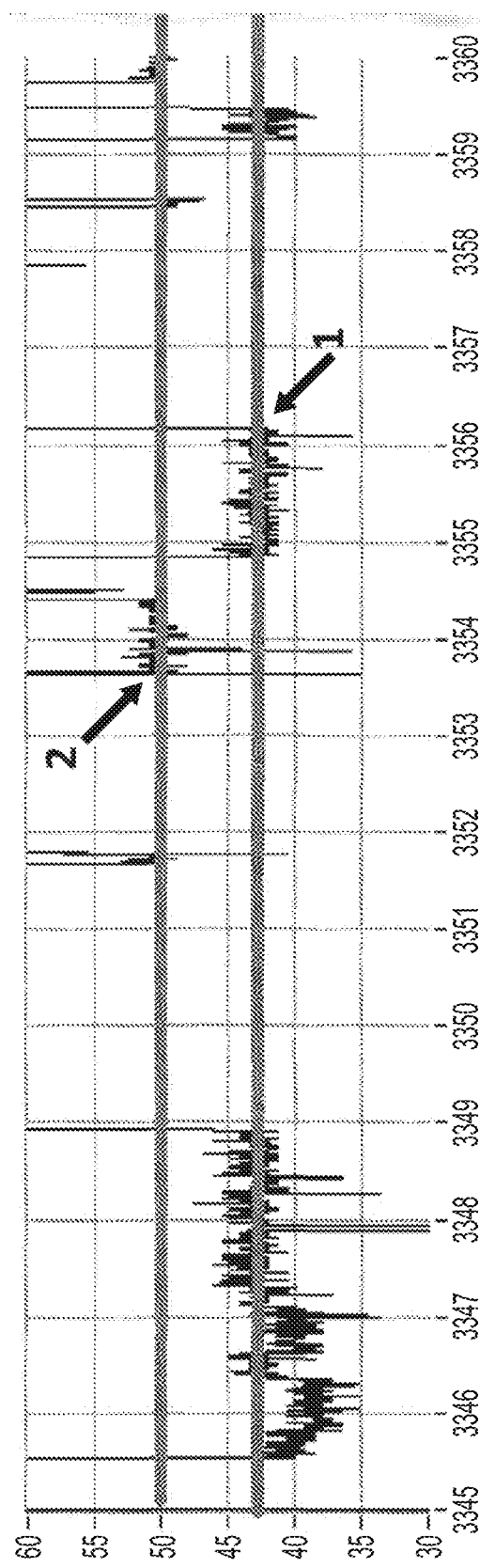
FIG. 15 shows an expanded view of the different block levels that are observed for aptamer sequence strep probe 1 (SEQ ID NO: 24) in the presence (2) and absence (1) of streptavidin (the y-axis=current (pA) and the x-axis=time (s)). This data has been Bessel filtered for presentation purposes.
Figure 16:
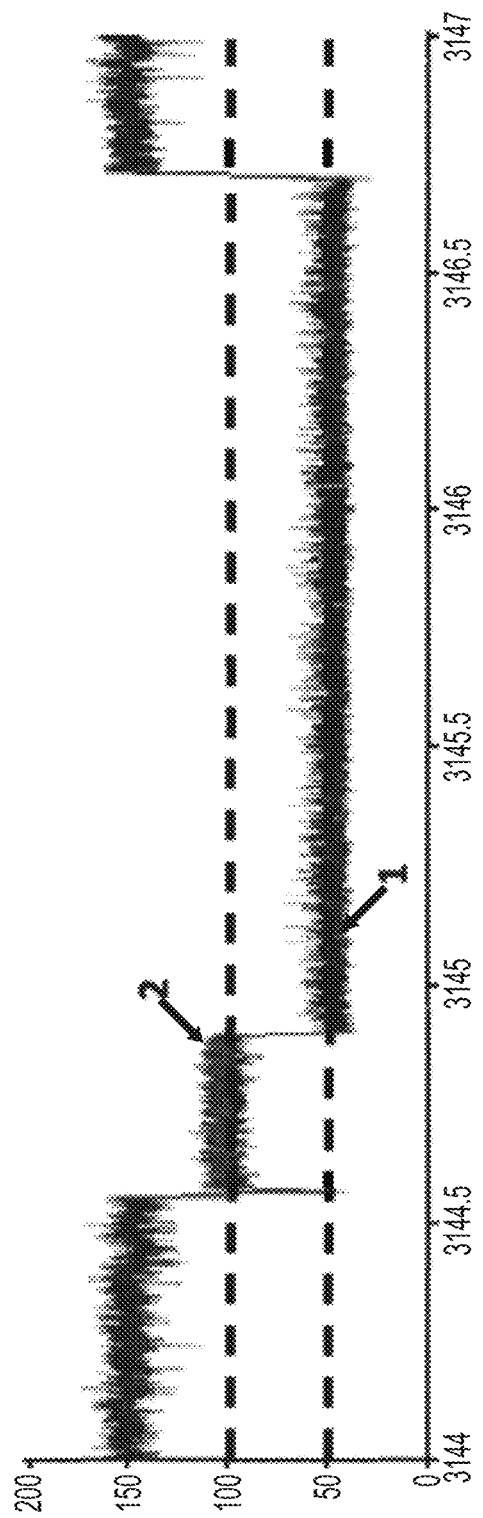
FIG. 16 illustrates an example block level observed for aptamer sequence 27x3A_TBA in the presence of thrombin (the y-axis=current (pA) and the x-axis=time (s)) in a solution of 20% whole rabbit blood in K2 EDTA (Harlan Scientific, code—S.B-0009) 80% buffer (625 mM KCl, 100 mM HEPES, 75 mM potassium ferrocyanide, 25 mM potassium ferricyanide pH8.0). Levels 1 and 2 are detected when the aptamer (sequence 27x3A_TBA) and thrombin are present in solution. The appearance of level 2 indicates aptamer bound to thrombin, and transitions from level 2 to level 1 indicate dissociation of the aptamer-thrombin complex.
Figure 17:
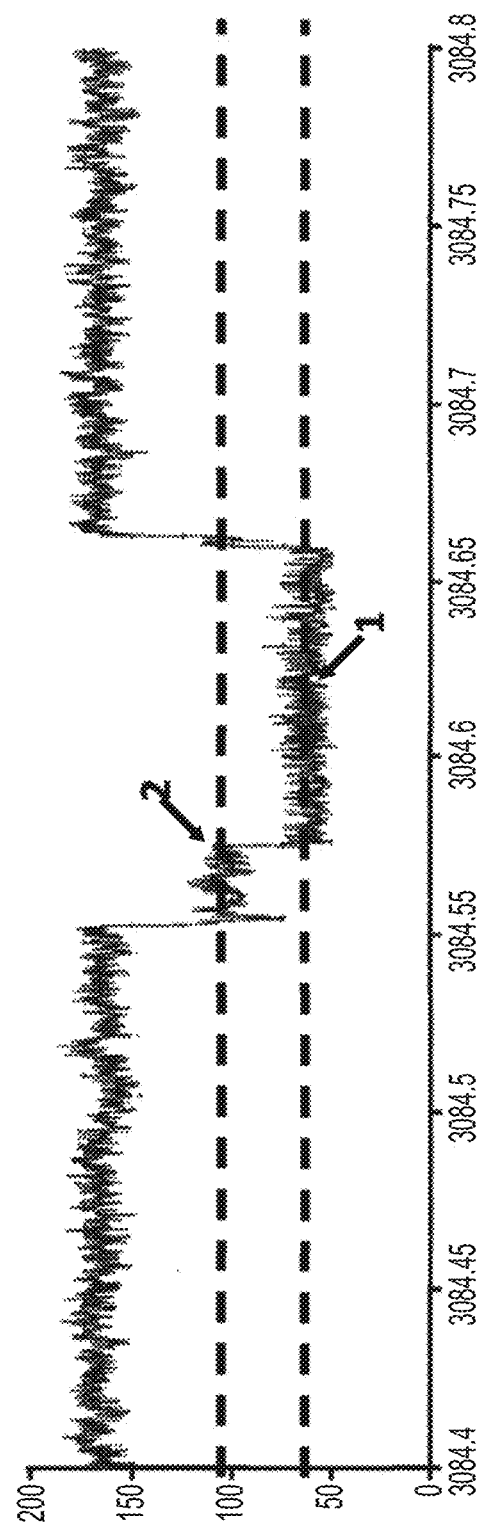
FIG. 17 illustrates an example block level observed for aptamer sequence 17x8A_PDGF in the presence of PDGF (the y-axis=current (pA) and the x-axis=time (s)) in a solution of 20% whole rabbit blood in K2 EDTA (Harlan Scientific, code—S.B-0009) 80% buffer (625 mM KCl, 100 mM HEPES, 75 mM potassium ferrocyanide, 25 mM potassium ferricyanide pH8.0). Levels 1 and 2 are detected when the aptamer (sequence 17x8A_PDGF) and PDGF are present in solution. The appearance of level 2 indicates aptamer bound to PDGF, and transitions from level 2 to level 1 indicate dissociation of the aptamer-PDGF complex.
Figure 18:
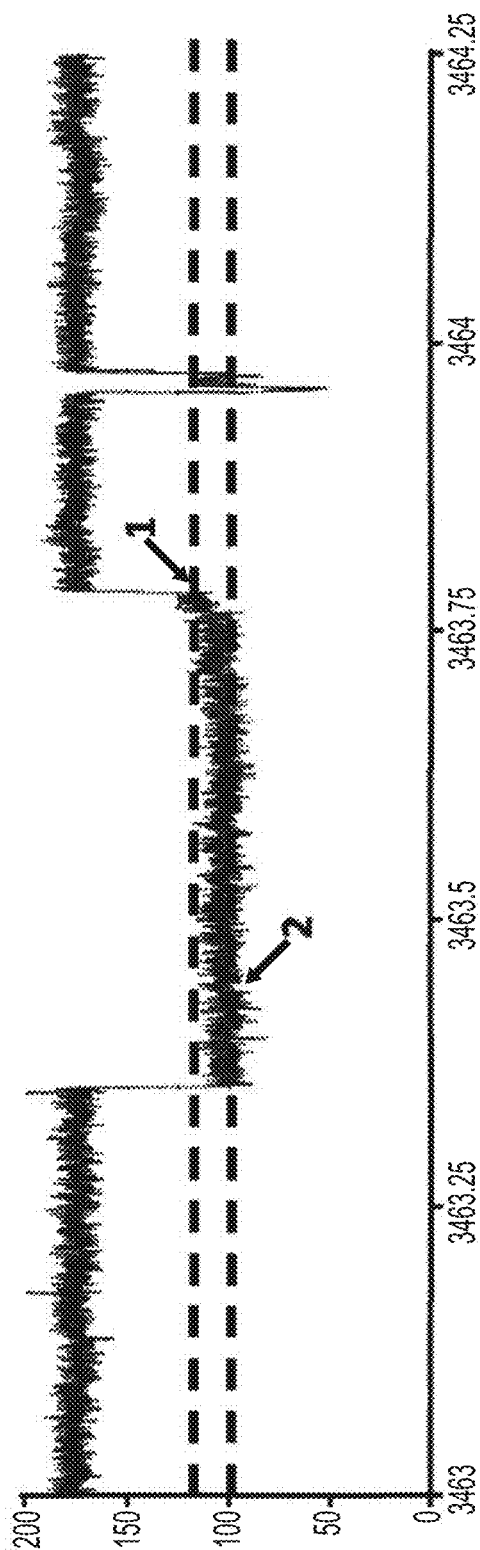
FIG. 18 illustrates an example block level observed for aptamer sequence 25x_ATP in the presence of ATP (the y-axis=current (pA) and the x-axis=time (s)) in a solution of 20% whole rabbit blood in K2 EDTA (Harlan Scientific, code—S.B-0009) 80% buffer (625 mM KCl, 100 mM HEPES, 75 mM potassium ferrocyanide, 25 mM potassium ferricyanide pH8.0). Levels 1 and 2 are detected when the aptamer (sequence 25x_ATP) and ATP are present in solution. The appearance of level 2 indicates aptamer bound to ATP, and transitions from level 2 to level 1 indicate dissociation of the aptamer-ATP complex.

Using the above method it was possible to detect characteristic block levels in the presence (FIG. 14B) and absence (FIG. 14A) of streptavidin. Upon the addition of the strep probe 1 (SEQ ID NO: 24) only a block level at level 1 was observed (see FIG. 14A). Whereas, when the strep probe 1 had been pre-incubated with streptavidin an additional level (level 2; FIG. 14B) was also detected. FIG. 15 shows an expanded view of the different block levels that are observed for aptamer sequence strep probe 1 (SEQ ID NO: 24) in the presence (2) and absence (1) of streptavidin (the y-axis=current (pA) and the x-axis=time (s)). This has been Bessel filtered for presentation purposes.

Example 12

This example illustrates how a nanopore can detect the presence of the proteins thrombin, PDGF and ATP in a sample containing 20% whole rabbit blood in K2 EDTA (Harlan Scientific, code—S.B-0009).

Materials and Methods

Electrical measurements are acquired using the standard 128 well silicon chips (format 75 µm diameter, 20 µm depth and 250 um pitch) which are platinum plated (WO 2009/077734). In order to carry-out experiments which allow detection of the presence of the proteins thrombin, PDGF and ATP in a sample which contains 20% whole rabbit blood in K2 EDTA (Harlan Scientific, code—S.B-0009), the same experimental set-up procedure is performed as described in Example 1 (using the nanopore αHL-(E111N/K147N)$_7$ (NN) and buffer 625 mM KCl, 100 mM HEPES, 75 mM potassium ferrocyanide, 25 mM potassium ferricyanide pH8.0), with the same initial control programme (10 seconds at 0 mV, 50 seconds at 170 mV—repeated up to 20 times) run for 3 minutes.

After three minutes the script is stopped and 27x3A_TBA (SEQ ID NO: 16, 125 nM), 17x8A_PDGF (SEQ ID NO: 20, 125 nM) and 25x_ATP (SEQ ID NO: 22, 125 nM), thrombin (1 µM) (Cat No. T6884, Sigma-Aldrich, Dorset, UK), PDGF (1 µM) and ATP (10 mM) which are pre-incubated together, before addition to the chamber for a minimum of 5 minutes in 20%>whole rabbit blood in K2 EDTA (Harlan Scientific, code—S.B-0009) 80% buffer (625 mM KCl, 100 mM HEPES, 75 mM potassium ferrocyanide, 25 mM potassium ferricyanide pH8.0), are flowed into the chamber and the control programme run. At the end of the experiment the control programme is stopped.

Discussion

Using the above method it is possible to detect characteristic step level changes for all three analytes when present in 20% whole rabbit blood in K2 EDTA (Harlan Scientific, code—S.B-0009) 80% buffer solutions.

The invention claimed is:

1. A multiplex assay method for determining the presence of at least one aptamer in a solution, the method comprising:
(a) contacting a transmembrane pore with a solution comprising a plurality of aptamers, each aptamer being folded into a three-dimensional structure, wherein each aptamer in the plurality is conjugated to a linear, single-stranded polynucleotide tail, wherein each linear, single-stranded polynucleotide tail that is conjugated to an aptamer in the plurality is different than each other linear, single-stranded polynucleotide tail that is conjugated to an aptamer in the plurality, and wherein each linear, single-stranded polynucleotide tail enters the pore and affects current flow through the pore;

(b) applying an electrical potential across the pore, wherein the linear, single-stranded polynucleotide tail of at least two aptamers each enters the pore, in succession, and each affects current flow through the pore, wherein movement of each linear, single-stranded polynucleotide tail through the pore produces a distinct current flow that is different than current flow through the pore produced by the other linear, single-stranded polynucleotide tails, and each aptamer unfolds under the influence of the potential and then moves through the pore after its linear, single-stranded polynucleotide tail;

(c) successively measuring current flowing through the pore as each linear, single-stranded polynucleotide tail of each aptamer of step (b) enters the pore; and (d) determining the presence of each aptamer conjugated to each linear, single-stranded polynucleotide tail based on the distinct current flow through the pore caused by the linear, single-stranded polynucleotide tail of step (b).

2. A method according to claim 1, wherein at least one tail comprises residues 1 to 30 of any one of SEQ ID Nos: 7 to 23.

3. A method according to claim 1, wherein each tail is a linear, single-stranded polynucleotide from 7 to 70 nucleotides in length.

4. A method according to claim 1, wherein each aptamer is a peptide aptamer or an oligonucleotide aptamer.

5. A method according to claim 1, wherein the transmembrane pore comprises a vestibule and a barrel, optionally wherein:

(a) the barrel is sufficiently narrow that a double-stranded polynucleotide cannot pass through the transmembrane pore; or (b) the vestibule and barrel are each long enough to contain at least two nucleotides; or (c) the pore is a transmembrane protein pore or a solid state pore.

6. A method according to claim 5, wherein the transmembrane protein pore is α-hemolysin, leukocidin, *Mycobacterium smegmatis* porin A (MspA), outer membrane phospholipase A, *Neisseria* autotransporter lipoprotein (NalP) and is optionally (a) formed of seven identical subunits, wherein each subunit comprises the sequence shown in SEQ ID NO: 2; or (b) a variant thereof in which one or more of the seven subunits has at least 50% homology to SEQ ID NO: 2 based on amino acid identify over the entire sequence and which retains pore activity; or (c) α-hemolysin formed of four identical subunits as shown in SEQ ID NO: 4 and four identical subunits as shown in SEQ ID NO: 6; or (d) a variant thereof in which one or more of the subunits has at least 50% homology to SEQ ID NO: 4 based on amino acid identity over the entire sequence and/or one or more of the subunits has at least 50% homology to SEQ ID NO: 6 based on amino acid identity over the entire sequence and the pore retains pore activity.

* * * * *

SEQUENCE LISTING

<160> NUMBER OF SEQ ID NOS: 24

<210> SEQ ID NO 1
<211> LENGTH: 885
<212> TYPE: DNA
<213> ORGANISM: Artificial sequence
<220> FEATURE:
<223> OTHER INFORMATION: Alpha-hemolysin mutant (E111N/K147N)

<400> SEQUENCE: 1

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaaactgc tagttattag aacaaaaggt    180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaaaactata tgagtacttt aacttatgga    360
ttcaacggta atgttactgg tgatgataca ggaaaaattg gcggccttat tggtgcaaat    420
gtttcgattg gtcatacact gaactatgtt caacctgatt caaaacaat tttagagagc     480
ccaactgata aaaagtagg ctggaaagtg atatttaaca atatggtgaa tcaaaattgg     540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agactccgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                    885
```

<210> SEQ ID NO 2
<211> LENGTH: 293
<212> TYPE: PRT
<213> ORGANISM: Artificial sequence
<220> FEATURE:
<223> OTHER INFORMATION: Alpha-hemolysin mutant (E111N/K147N)

<400> SEQUENCE: 2

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140
```

```
Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 903
<212> TYPE: DNA
<213> ORGANISM: Artificial sequence
<220> FEATURE:
<223> OTHER INFORMATION: LukF subunit of gamma-hemolysin

<400> SEQUENCE: 3
atggcggaag gcaaaattac cccggttagc gtgaaaaaag ttgatgacaa agtgaccctg      60
tataaaacga cggcgacggc ggatagcgat aaatttaaaa ttagccagat cctgaccttc     120
aacttcatca agacaaatc ttatgataaa gacaccctgg ttctgaaagc gacgggcaac     180
atcaatagcg gttttgtcaa accgaacccg aatgattacg acttctcaaa actgtattgg     240
ggcgccaaat acaatgtctc gattagctct cagagtaacg attccgtgaa tgcggttgac     300
tatgccccga aaaccaaaa cgaagaattc caggttcaaa cacccctggg ttacacgttc     360
ggcggtgata tttcaatctc gaatggcctg agtggcggtc tgaacggtaa taccgcattt     420
tccgaaacga ttaactataa acaggaaagc taccgtaccc tgtctcgcaa cacgaattat     480
aaaaacgtcg gctggggtgt ggaagcgcat aaaatcatga atggctgggg tccgtatggc     540
cgtgattcct ttcacccgac ctacggcaac gaactgttcc tggcaggtcg ccagagttcc     600
gcgtatgccg gtcaaaattt tattgctcag catcaaatgc cgctgctgag ccgttctaac     660
tttaatccgg aattcctgtc agtgctgtcg caccgtcagg atcgcgcgaa aaaatctaaa     720
atcaccgtta cgtaccagcg tgaaatggac ctgtaccaaa tccgctggaa tggcttctat     780
tgggcaggtg ctaactacaa aaattttaaa acccgcacgt tcaaatctac ctatgaaatc     840
gattgggaaa atcacaaagt caaactgctg acaccaaag aaaccgaaaa caacaaataa     900
taa                                                                   903

<210> SEQ ID NO 4
<211> LENGTH: 298
<212> TYPE: PRT
<213> ORGANISM: Artificial sequence
<220> FEATURE:
<223> OTHER INFORMATION: LukF subunit of gamma-hemolysin
```

<400> SEQUENCE: 4

| | | | | | | | | | | | | | | |
|---|---|---|---|---|---|---|---|---|---|---|---|---|---|---|
| Ala | Glu | Gly | Lys | Ile | Thr | Pro | Val | Ser | Val | Lys | Val | Asp | Asp | Lys |
| 1 | | | | 5 | | | | | 10 | | | | | 15 |
| Val | Thr | Leu | Tyr | Lys | Thr | Thr | Ala | Thr | Ala | Asp | Ser | Asp | Lys | Phe | Lys |
| | | | 20 | | | | | 25 | | | | | 30 | | |
| Ile | Ser | Gln | Ile | Leu | Thr | Phe | Asn | Phe | Ile | Lys | Asp | Lys | Ser | Tyr | Asp |
| | | 35 | | | | | 40 | | | | | 45 | | | |
| Lys | Asp | Thr | Leu | Val | Leu | Lys | Ala | Thr | Gly | Asn | Ile | Asn | Ser | Gly | Phe |
| | 50 | | | | | 55 | | | | | 60 | | | | |
| Val | Lys | Pro | Asn | Pro | Asn | Asp | Tyr | Asp | Phe | Ser | Lys | Leu | Tyr | Trp | Gly |
| 65 | | | | 70 | | | | | 75 | | | | | 80 | |
| Ala | Lys | Tyr | Asn | Val | Ser | Ile | Ser | Ser | Gln | Ser | Asn | Asp | Ser | Val | Asn |
| | | | | 85 | | | | | 90 | | | | | 95 | |
| Ala | Val | Asp | Tyr | Ala | Pro | Lys | Asn | Gln | Asn | Glu | Glu | Phe | Gln | Val | Gln |
| | | | 100 | | | | | 105 | | | | | 110 | | |
| Asn | Thr | Leu | Gly | Tyr | Thr | Phe | Gly | Gly | Asp | Ile | Ser | Ile | Ser | Asn | Gly |
| | | 115 | | | | | 120 | | | | | 125 | | | |
| Leu | Ser | Gly | Gly | Leu | Asn | Gly | Asn | Thr | Ala | Phe | Ser | Glu | Thr | Ile | Asn |
| | 130 | | | | | 135 | | | | | 140 | | | | |
| Tyr | Lys | Gln | Glu | Ser | Tyr | Arg | Thr | Leu | Ser | Arg | Asn | Thr | Asn | Tyr | Lys |
| 145 | | | | | 150 | | | | | 155 | | | | | 160 |
| Asn | Val | Gly | Trp | Gly | Val | Glu | Ala | His | Lys | Ile | Met | Asn | Gly | Trp | Gly |
| | | | | 165 | | | | | 170 | | | | | 175 | |
| Pro | Tyr | Gly | Arg | Asp | Ser | Phe | His | Pro | Thr | Tyr | Gly | Asn | Glu | Leu | Phe |
| | | | 180 | | | | | 185 | | | | | 190 | | |
| Leu | Ala | Gly | Arg | Gln | Ser | Ser | Ala | Tyr | Ala | Gly | Gln | Asn | Phe | Ile | Ala |
| | | 195 | | | | | 200 | | | | | 205 | | | |
| Gln | His | Gln | Met | Pro | Leu | Leu | Ser | Arg | Ser | Asn | Phe | Asn | Pro | Glu | Phe |
| | 210 | | | | | 215 | | | | | 220 | | | | |
| Leu | Ser | Val | Leu | Ser | His | Arg | Gln | Asp | Arg | Ala | Lys | Lys | Ser | Lys | Ile |
| 225 | | | | | 230 | | | | | 235 | | | | | 240 |
| Thr | Val | Thr | Tyr | Gln | Arg | Glu | Met | Asp | Leu | Tyr | Gln | Ile | Arg | Trp | Asn |
| | | | | 245 | | | | | 250 | | | | | 255 | |
| Gly | Phe | Tyr | Trp | Ala | Gly | Ala | Asn | Tyr | Lys | Asn | Phe | Lys | Thr | Arg | Thr |
| | | | 260 | | | | | 265 | | | | | 270 | | |
| Phe | Lys | Ser | Thr | Tyr | Glu | Ile | Asp | Trp | Glu | Asn | His | Lys | Val | Lys | Leu |
| | | 275 | | | | | 280 | | | | | 285 | | | |
| Leu | Asp | Thr | Lys | Glu | Thr | Glu | Asn | Asn | Lys | | | | | | |
| | 290 | | | | | 295 | | | | | | | | | |

<210> SEQ ID NO 5
<211> LENGTH: 849
<212> TYPE: DNA
<213> ORGANISM: Artificial sequence
<220> FEATURE:
<223> OTHER INFORMATION: Hlg2 subunit of gamma-hemolysin

<400> SEQUENCE: 5

```
atggaaaaca aaatcgaaga catcggtcaa ggcgctgaaa tcatcaaacg cacgcaggac      60
attacctcta acgtctggc tattacccag aatattcaat tcgatttcgt gaaagacaaa     120
aaatacaaca agatgcact ggtggttaaa atgcagggct ttatcagctc tcgtaccacg     180
tacagcgatc tgaaaaaata tccgtacatt aaacgcatga tctggccgtt ccagtacaac     240
attagtctga aaccaaaga ttccaacgtg gacctgatta ttacctgcc gaaaaacaaa     300
```

-continued

```
atcgatagtg cggacgtttc ccagaaactg gctataaca ttggcggtaa ttttcaatca    360
gccccgtcga tcggcggtag tggttccttc aattactcaa aaaccatctc gtacaaccag    420
aaaaattacg ttacggaagt cgaaagccaa aactctaaag gcgtgaaatg gggtgttaaa    480
gcgaattcat ttgtcacccc gaacggccag gtgtcggcgt atgatcagta cctgtttgca    540
caagacccga cgggtccggc agcacgtgat tatttcgttc cggacaatca gctgccgccg    600
ctgattcaaa gcggctttaa cccgtctttc atcaccacgc tgtcccatga acgtggcaaa    660
ggtgataaaa gcgaatttga aattaccctat ggtcgcaaca tggatgcaac ctatgcttac    720
gttacgcgtc atcgcctggc agtcgatcgt aaacacgacg ctttcaaaaa ccgcaatgtc    780
accgtgaaat acgaagtcaa ctggaaaacg cacgaagtca aaatcaaaag tatcacgccg    840
aaataataa                                                              849
```

<210> SEQ ID NO 6
<211> LENGTH: 280
<212> TYPE: PRT
<213> ORGANISM: Artificial sequence
<220> FEATURE:
<223> OTHER INFORMATION: Hlg2 subunit of gamma-hemolysin

<400> SEQUENCE: 6

```
Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
    50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
                85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
        115                 120                 125

Phe Asn Tyr Ser Lys Thr Ile Ser Tyr Asn Gln Lys Asn Tyr Val Thr
    130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
        195                 200                 205

Phe Ile Thr Thr Leu Ser His Glu Arg Gly Lys Gly Asp Lys Ser Glu
    210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255
```

Arg Asn Val Thr Val Lys Tyr Glu Val Asn Trp Lys Thr His Glu Val
            260                 265                 270

Lys Ile Lys Ser Ile Thr Pro Lys
        275                 280

<210> SEQ ID NO 7
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (6)..(20)
<223> OTHER INFORMATION: n = abasic nucleotide

<400> SEQUENCE: 7
aaaaannnnn nnnnnnnnnn aaaaaaaaaa ggttggtgtg gttgg                45

<210> SEQ ID NO 8
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(11)
<223> OTHER INFORMATION: n = abasic nucleotide

<400> SEQUENCE: 8
nnnnnnnnnn naaaaaaaaa aaaaaaaaaa ggttggtgtg gttgg                45

<210> SEQ ID NO 9
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(13)
<223> OTHER INFORMATION: n = abasic nucleotide

<400> SEQUENCE: 9
nnnnnnnnnn nnnaaaaaaa aaaaaaaaaa ggttggtgtg gttgg                45

<210> SEQ ID NO 10
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(15)
<223> OTHER INFORMATION: n = abasic nucleotide

<400> SEQUENCE: 10
nnnnnnnnnn nnnnnaaaaa aaaaaaaaaa ggttggtgtg gttgg                45

<210> SEQ ID NO 11
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(17)
<223> OTHER INFORMATION: n = abasic nucleotide

<400> SEQUENCE: 11
nnnnnnnnnn nnnnnnnaaa aaaaaaaaaa ggttggtgtg gttgg         45

<210> SEQ ID NO 12
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(19)
<223> OTHER INFORMATION: n = abasic nucleotide

<400> SEQUENCE: 12
nnnnnnnnnn nnnnnnnna aaaaaaaaaa ggttggtgtg gttgg         45

<210> SEQ ID NO 13
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(21)
<223> OTHER INFORMATION: n = abasic nucleotide

<400> SEQUENCE: 13
nnnnnnnnnn nnnnnnnnnn naaaaaaaaa ggttggtgtg gttgg         45

<210> SEQ ID NO 14
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_featurre
<222> LOCATION: (1)..(23)
<223> OTHER INFORMATION: n = abasic nucleotide
<220> FEATURE:
<221> NAME/KEY: misc_feature
<222> LOCATION: (1)..(23)
<223> OTHER INFORMATION: n is a, c, g, or t

<400> SEQUENCE: 14
nnnnnnnnnn nnnnnnnnnn nnnaaaaaaa ggttggtgtg gttgg         45

<210> SEQ ID NO 15
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(25)
<223> OTHER INFORMATION: n = abasic nucleotide

<400> SEQUENCE: 15
nnnnnnnnnn nnnnnnnnnn nnnnnaaaaa ggttggtgtg gttgg         45

<210> SEQ ID NO 16
<211> LENGTH: 45
<212> TYPE: DNA

```
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(27)
<223> OTHER INFORMATION: n = abasic nucleotide

<400> SEQUENCE: 16
nnnnnnnnnn nnnnnnnnnn nnnnnnnaaa ggttggtgtg gttgg            45

<210> SEQ ID NO 17
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(29)
<223> OTHER INFORMATION: n = abasic nucleotide

<400> SEQUENCE: 17
nnnnnnnnnn nnnnnnnnnn nnnnnnnnna ggttggtgtg gttgg            45

<210> SEQ ID NO 18
<211> LENGTH: 45
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(30)
<223> OTHER INFORMATION: n = abasic nucleotide

<400> SEQUENCE: 18
nnnnnnnnnn nnnnnnnnnn nnnnnnnnnn ggttggtgtg gttgg            45

<210> SEQ ID NO 19
<211> LENGTH: 100
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (25)..(33)
<223> OTHER INFORMATION: n = abasic nucleotide

<400> SEQUENCE: 19
aaaaaaaaac aaaaaaaaaa aaaannnnnn nnnaaaaaaa ggttggtgtg gttggaaaaa    60
aaaaaaaaaa caaaaaaaaa aaaaaacaaa aaaaaaaaa                          100

<210> SEQ ID NO 20
<211> LENGTH: 60
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(17)
<223> OTHER INFORMATION: n = abasic nucleotide

<400> SEQUENCE: 20
nnnnnnnnnn nnnnnnnaaa aaaaacaggc tacggcacgt agagcatcac catgatcctg    60
```

```
<210> SEQ ID NO 21
<211> LENGTH: 60
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(25)
<223> OTHER INFORMATION: n = abasic nucleotide

<400> SEQUENCE: 21
nnnnnnnnnn nnnnnnnnnn nnnnncaggc tacggcacgt agagcatcac catgatcctg    60

<210> SEQ ID NO 22
<211> LENGTH: 51
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(25)
<223> OTHER INFORMATION: n = abasic nucleotide

<400> SEQUENCE: 22
nnnnnnnnnn nnnnnnnnnn nnnnnacctg ggggagtatt gcggaggaag g    51

<210> SEQ ID NO 23
<211> LENGTH: 51
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (1)..(17)
<223> OTHER INFORMATION: n = abasic nucleotide

<400> SEQUENCE: 23
nnnnnnnnnn nnnnnnnaaa aaaaaacctg ggggagtatt gcggaggaag g    51

<210> SEQ ID NO 24
<211> LENGTH: 66
<212> TYPE: DNA
<213> ORGANISM: Artificial Sequence
<220> FEATURE:
<223> OTHER INFORMATION: Sequence included in the examples
<220> FEATURE:
<221> NAME/KEY: misc_feature
<222> LOCATION: (61)..(61)
<223> OTHER INFORMATION: n = abasic nucleotide
<220> FEATURE:
<221> NAME/KEY: misc_feature
<222> LOCATION: (63)..(63)
<223> OTHER INFORMATION: n = abasic nucleotide
<220> FEATURE:
<221> NAME/KEY: misc_feature
<222> LOCATION: (65)..(65)
<223> OTHER INFORMATION: n = abasic nucleotide

<400> SEQUENCE: 24
ctatactcca ctttgctatt tctcggttcc ttcacgcgcc gatcgcaggc tgatgaattg    60 ntntnt    66
```